United States Patent
Bakthavatchalam

(10) Patent No.: US 6,630,476 B2
(45) Date of Patent: Oct. 7, 2003

(54) PYRROLO [3,4-D] PYRIMIDINES AS CORTICOTROPIN RELEASING FACTOR (CRF) ANTAGONISTS

(75) Inventor: Rajagopal Bakthavatchalam, Branford, CT (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 09/898,326

(22) Filed: Jul. 3, 2001

(65) Prior Publication Data

US 2002/0022632 A1 Feb. 21, 2002

Related U.S. Application Data

(60) Provisional application No. 60/216,887, filed on Jul. 7, 2000.

(51) Int. Cl.[7] .................... A61K 31/519; C07D 487/00; C07D 487/02
(52) U.S. Cl. ................ 514/258; 514/412; 514/428; 544/280; 544/335; 548/453; 548/460; 548/484
(58) Field of Search ................ 514/258, 412, 514/428; 544/280, 335; 548/453, 466, 484

(56) References Cited

U.S. PATENT DOCUMENTS

| | | | |
|---|---|---|---|
| 3,910,907 A | 10/1975 | O'Brien | 260/248 |
| 3,995,039 A | 11/1976 | Rooney et al. | 424/249 |
| 4,567,263 A | 1/1986 | Eicken et al. | 544/263 |
| 4,621,556 A | 11/1986 | Soltysiak et al. | 831/670 |
| 4,892,576 A | 1/1990 | Kruger et al. | 71/93 |
| 4,997,940 A | 3/1991 | Vinogradoff et al. | 544/281 |
| 5,137,887 A | 8/1992 | Hashimoto et al. | 514/240 |
| 5,397,774 A | 3/1995 | Nugent et al. | 514/81 |
| 5,484,760 A | 1/1996 | Bussler et al. | 504/103 |
| 5,861,385 A | 1/1999 | Angerbauer et al. | 514/140 |

FOREIGN PATENT DOCUMENTS

| | | |
|---|---|---|
| DE | 4243279 | 6/1994 |
| EP | 0269859 | 6/1988 |
| EP | 0374448 | 6/1990 |
| EP | 0511528 | 11/1992 |
| EP | 0521622 | 1/1993 |
| EP | 0531901 | 3/1993 |
| EP | 0591528 | 4/1994 |
| EP | 0594149 | 4/1994 |
| EP | 0662477 | 7/1995 |
| EP | 0778277 | 6/1997 |
| WO | WO 92/10098 | 6/1992 |
| WO | WO 95/10506 | 4/1995 |
| WO | WO 95/35298 | 6/1995 |
| WO | WO 95/33727 | 12/1995 |
| WO | 9533750 | * 12/1995 |
| WO | WO 95/33750 | 12/1995 |
| WO | WO 95/34563 | 12/1995 |
| WO | WO 98/08847 | 3/1998 |
| WO | WO 98/29397 | 7/1998 |
| WO | WO 99/51599 | 10/1999 |

OTHER PUBLICATIONS

J. Rivier et al., Proc. Nat. Acad. Sci., 80:4851 (1983).
W. Vale et al., Science, 213:1394 (1981).
W. Vale et al., Rec. Prog. Horm. Res., 39:245 (1983).
G.F. Koob, Persp. Behav. Med., 2:39 (1985).
E.B. Desouza et al., J. Neuroscience, 5:3189 (1985).
J.E. Blalock, Physiological Review, 69:1 (1989).
J.E. Morley, Life Science, 41:527 (1987).
E. B. Desouza, Hosp. Practice, 23:59 (1988).
C.B. Nemeroff et al., Science, 226:1342 (1984).
C.M. Banki et al., Am. J. Psychiatry, 144:873 (1987).
R.D. France et al., Biol. Psychiatry, 23:86 (1988).
M. Arato et al, Biol. Psychiatry, 25:355 (1989).
C.B. Nemeroff et al., Arch. Gen. Psychiatry, 45:577 (1988).
P.W. Gold et al., Am. J. Psychiatry, 141:619 (1984).
F. Holsboer et al., Psychoneuroendocrinology, 9:147 (1984).
P.W. Gold et al., New Eng. J. Med., 314:1129 (1986).
R.M. Sapolsky, Arch. Gen. Psychiatry, 46:1047 (1989).
Grigoriadis et al., Neuropsychopharmacology, 2:53 (1989).
D.R. Britton et al., Life Science, 31:363 (1982).
C.W. Berridge & A.J. Dunn, Regul. Peprides, 16:83 (1986).
C.W. Berridge & A.J. Dunn, Horm. Behavior, 21:393 (1987).
Brain Research Reviews, 15:71 (1990).
K.T. Britton et al., Psychopharmacology, 86:170 (1985).
K.T. Britton et al., Psychopharmacology, 94:306 (1988).

(List continued on next page.)

Primary Examiner—Richard L. Raymond
Assistant Examiner—Sudhaker B. Patel
(74) Attorney, Agent, or Firm—Shah R. Makujina; Kalim S. Fuzail; Woodcock Washburn LLP

(57) ABSTRACT

Corticotropin releasing factor (CRF) antagonists of Formula (I) or (II)

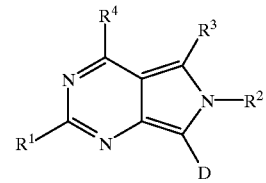

(I)

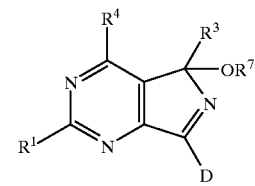

(II)

and their use in treating anxiety, depression, and other psychiatric, neurological disorders as well as treatment of immunological, cardiovascular or heart-related diseases and colonic hypersensitivity associated with psychopathological disturbance and stress.

8 Claims, No Drawings

OTHER PUBLICATIONS

N.R. Swerdlow et al., Psychopharmacology, 88:147 (1986).
Koob & Britton, Basic & Clinical Studies of a Neuropeptide, De Souza & Nemeroff eds., p 221 (1990).
Senga et al., J. Med. Chem., 1982, 25, 2430249.
Springer et al., J. Med. Chem., 1976, vol. 19, No. 2, 291–296.
Josi et al., J. Prakt. Chemie, 321, 2, 1979, 341–344.
Maquestiau et al., Bull. Soc. Belg., vol 101, No. 2, 1982, pp 131–136.
Ibrahim et al., Arch. Pharm., 320, 487–491 (1987).
J. Med. Chem., 24, 610–613 (1981).
J. Het. Chem., 22, 601 (1985).
Database WPI, Week 200037, Derwent Publications Ltd, London, GB, AN 1998–388003, XP002188632.

* cited by examiner

PYRROLO [3,4-D] PYRIMIDINES AS CORTICOTROPIN RELEASING FACTOR (CRF) ANTAGONISTS

CROSS-REFERENCE TO RELATED APPLICATIONS

This application claims the benefit of U.S. Provisional Application No. 60/216,887 filed Jul. 7, 2000.

FIELD OF THE INVENTION

This invention relates a treatment of psychiatric disorders and neurological diseases including major depression, anxiety-related disorders, post-traumatic stress disorder, supranuclear palsy and feeding disorders as well as treatment of immunological, cardiovascular or heart-related diseases and colonic hypersensitivity associated with psychopathological disturbance and stress, by administration of certain pyrrolo[3,4-d]pyrimidines.

BACKGROUND OF THE INVENTION

Corticotropin releasing factor (herein referred to as CRF), a 41 amino acid peptide, is the primary physiological regulator of proopiomelanocortin(POMC)—derived peptide secretion from the anterior pituitary gland [J. Rivier et al., Proc. Nat. Acad. Sci. (USA) 80:4851 (1983); W. Vale et al., Science 213:1394 (1981)]. In addition to its endocrine role at the pituitary gland, immunohistochemical localization of CRF has demonstrated that the hormone has a broad extra-hypothalamic distribution in the central nervous system and produces a wide spectrum of autonomic, electrophysiological and behavioral effects consistent with a neurotransmitter or neuromodulator role in brain [W. Vale et al., Rec. Prog. Horm. Res. 39:245 (1983); G. F. Koob, Persp. Behav. Med. 2:39 (1985); E. B. De Souza et al., J. Neurosci. 5:3189 (1985)]. There is also evidence that CRF plays a significant role in integrating the response of the immune system to physiological, psychological, and immunological stressors [J. E. Blalock, Physiological Reviews 69:1 (1989); J. E. Morley, Life Sci. 41:527 (1987)].

Clinical data provide evidence that CRF has a role in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis as they relate to the dysfunction of CRF neurons in the central nervous system [for review see E. B. De Souza, Hosp. Practice 23:59 (1988)].

In affective disorder, or major depression, the concentration of CRF is significantly increased in the cerebral spinal fluid (CSF) of drug-free individuals [C. B. Nemeroff et al., Science 226:1342 (1984); C. M. Banki et al., Am. J. Psychiatry 144:873 (1987); R. D. France et al., Biol. Psychiatry 28:86 (1988); M. Arato et al., Biol Psychiatry 25:355 (1989)]. Furthermore, the density of CRF receptors is significantly decreased in the frontal cortex of suicide victims, consistent with a hypersecretion of CRF [C. B. Nemeroff et al., Arch. Gen. Psychiatry 45:577 (1988)]. In addition, there is a blunted adrenocorticotropin (ACTH) response to CRF (i.v. administered) observed in depressed patients [P. W. Gold et al., Am J. Psychiatry 141:619 (1984); F. Holsboer et al., Psychoneuroendocrinology 9:147 (1984); P. W. Gold et al., New Eng. J. Med. 314:1129 (1986)]. Preclinical studies in rats and non-human primates provide additional support for the hypothesis that hypersecretion of CRF may be involved in the symptoms seen in human depression [R. M. Sapolsky, Arch. Gen. Psychiatry 46:1047 (1989)]. There is preliminary evidence that tricyclic antidepressants can alter CRF levels and thus modulate the numbers of CRF receptors in brain [Grigoriadis et al., Neuropsychopharmacology 2:53 (1989)].

There has also been a role postulated for CRF in the etiology of anxiety-related disorders. CRF produces anxiogenic effects in animals and interactions between benzodiazepine/non-benzodiazepine anxiolytics and CRF have been demonstrated in a variety of behavioral anxiety models [D. R. Britton et al., Life Sci. 31:363 (1982); C. W. Berridge and A. J. Dunn Regul. Peptides 16:83 (1986)]. Preliminary studies using the putative CRF receptor antagonist a-helical ovine CRF (9-41) in a variety of behavioral paradigms demonstrate that the antagonist produces "anxiolytic-like" effects qualitatively similar to the benzodiazepines [C. W. Berridge and A. J. Dunn Horm. Behav. 21:393 (1987), Brain Research Reviews 15:71 (1990)]. Neurochemical, endocrine and receptor binding studies have all demonstrated interactions between CRF and benzodiazepine anxiolytics providing further evidence for the involvement of CRF in these disorders. Chlordiazepoxide attenuates the "anxiogenic" effects of CRF in both the conflict test [K. T. Britton et al., Psychopharmacology 86:170 (1985); K. T. Britton et al., Psychopharmacology 94:306 (1988)] and in the acoustic startle test [N. R. Swerdlow et al., Psychopharmacology 88:147 (1986)] in rats. The benzodiazepine receptor antagonist (Ro15-1788), which was without behavioral activity alone in the operant conflict test, reversed the effects of CRF in a dose-dependent manner while the benzodiazepine inverse agonist (FG7142) enhanced the actions of CRF [K. T. Britton et al., Psychopharmacology 94:306 (1988)].

The mechanisms and sites of action through which the standard anxiolytics and antidepressants produce their therapeutic effects remain to be elucidated. It has been hypothesized however, that they are involved in the suppression of the CRF hypersecretion that is observed in these disorders. Of particular interest is that preliminary studies examining the effects of a CRF receptor antagonist ($\alpha$-helical $CRF_{9-41}$) in a variety of behavioral paradigms have demonstrated that the CRF antagonist produces "anxiolytic-like" effects qualitatively similar to the benzodiazepines [for review see G. F. Koob and K. T. Britton, In: Corticotropin-Releasing Factor: Basic and Clinical Studies of a Neuropeptide, E. B. De Souza and C. B. Nemeroff eds., CRC Press p221 (1990)].

Several publications describe corticotropin releasing factor antagonist compounds and their use to treat psychiatric disorders and neurological diseases. Examples of such publications include DuPont Merck PCT application US94/11050, Pfizer WO 95/33750, Pfizer WO 95/34563, Pfizer WO 95/33727 and Pfizer EP 0778 277 A1.

Insofar as is known, [1,5-a]-pyrazolo-1,3,5-triazines, [1,5-a]-1,2,3-triazolo-1,3,5-triazines, [1,5-a]-pyrazolo-pyrimidines and [1,5-a]-1,2,3-triazolo-pyrimidines, have not been previously reported as corticotropin releasing factor antagonist compounds useful in the treatment of psychiatric disorders and neurological diseases. However, there have been publications which teach some of these compounds for other uses.

For instance, EP 0 269 859 (Ostuka, 1988) discloses pyrazolotriazine compounds of the formula

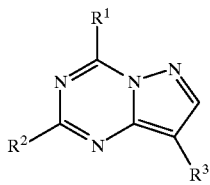

where $R^1$ is OH or alkanoyl, $R^2$ is H, OH, or SH, and $R^3$ is an unsaturated heterocyclic group, naphthyl or substituted phenyl, and states that the compounds have xanthine oxidase inhibitory activity and are useful for treatment of gout.

EP 0 594 149 (Ostuka, 1994) discloses pyrazolotriazine and pyrazolopyrimidine compounds of the formula

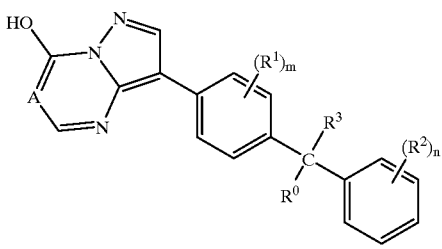

where A is CH or N, $R^0$ and $R^3$ are H or alkyl, and $R^1$ and $R^2$ are H, alkyl, alkoxyl, alkylthio, nitro, etc., and states that the compounds inhibit androgen and are useful in treatment of benign prostatic hypertrophy and prostatic carcinoma.

U.S. Pat. No. 3,910,907 (ICI, 1975) discloses pyrazolotriazines of the formula:

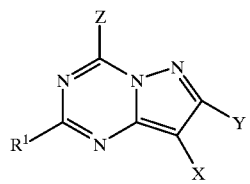

where R1 is $CH_3$, $C_2H_5$ or $C_6H_5$, X is H, $C_6H_5$, m-$CH_3C_6H_4$, CN, COOEt, Cl, I or Br, Y is H, $C_6H_5$, o-$CH_3C_6H_4$, or p-$CH_3C_6H_4$, and Z is OH, H, $CH_3$, $C_2H_5$, $C_6H_5$, n-$C_3H_7$, i-$C_3H_7$, SH, $SCH_3$, $NHC_4H_9$, or $N(C_2H_5)_2$, and states that the compounds are c-AMP phosphodiesterase inhibitors useful as bronchodilators.

U.S. Pat. No. 3,995,039 discloses pyrazolotriazines of the formula:

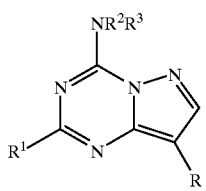

where $R^1$ is H or alkyl, $R^2$ is H or alkyl, $R^3$ is H, alkyl, alkanoyl, carbamoyl, or lower alkylcarbamoyl, and R is pyridyl, pyrimidinyl, or pyrazinyl, and states that the compounds are useful as bronchodilators.

U.S. Pat. No. 5,137,887 discloses pyrazolotriazines of the formula

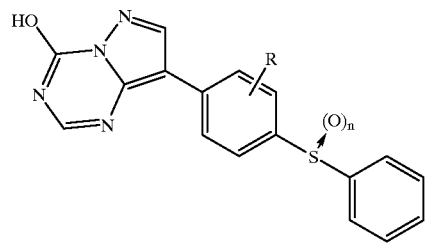

where R is lower alkoxy, and teaches that the compounds are xanthine oxidase inhibitors and are useful for treatment of gout.

U.S. Pat. No. 4,892,576 discloses pyrazolotriazines of the formula

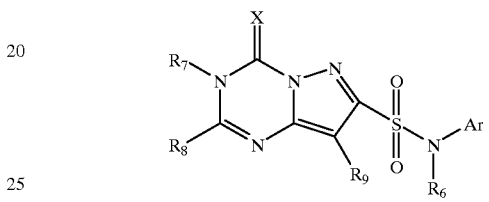

where X is O or S, Ar is a phenyl, naphthyl, pyridyl or thienyl group, $R_6$–$R_8$ are H, alkyl, etc., and $R_9$ is H, alkyl, phenyl, etc. The patent states that the compounds are useful as herbicides and plant growth regulants.

U.S. Pat. No. 5,484,760 and WO 92/10098 discloses herbicidal compositions containing, among other things, a herbicidal compound of the formula

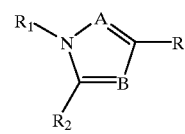

where A can be N, B can be $CR_3$, $R_3$ can be phenyl or substituted phenyl, etc., R is —$N(R_4)SO_2R_5$ or —$SO_2N(R_6)$ $R_7$ and $R_1$ and $R_2$ can be taken together to form

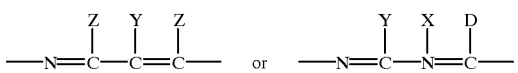

where X, Y and Z are H, alkyl, acyl, etc. and D is O or S.

U.S. Pat. No. 3,910,907 and Senga et al., J. Med. Chem., 1982, 25, 243–249, disclose triazolotriazines cAMP phosphodiesterase inhibitors of the formula

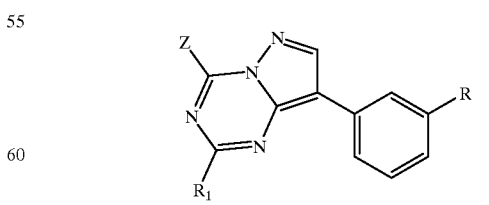

where Z is H, OH, $CH_3$, $C_2H_5$, $C_6H_5$, n-$C_3H_7$, iso-$C_3H_7$, SH, $SCH_3$, $NH(n-C_4H_9)$, or $N(C_2H_5)_2$, R is H or $CH_3$, and $R_1$ is $CH_3$ or $C_2H_5$. The reference lists eight therapeutic areas where inhibitors of cAMP phosphodiesterase could have utility: asthma, diabetes mellitus, female fertility control, male infertility, psoriasis, thrombosis, anxiety, and hypertension.

WO95/35298 (Otsuka, 1995) discloses pyrazolopyrimidines and states that they are useful as analgesics. The compounds are represented by the formula

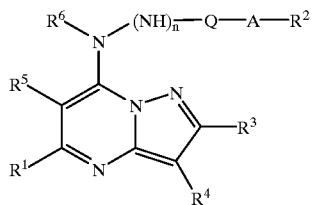

where Q is carbonyl or sulfonyl, n is 0 or 1, A is a single bond, alkylene or alkenylene, $R^1$ is H, alkyl, etc., $R^2$ is naphthyl, cycloalkyl, heteroaryl, substituted phenyl or phenoxy, $R^3$ is H, alkyl or phenyl, $R^4$ is H, alkyl, alkoxycarbonyl, phenylalkyl, optionally phenylthio-substituted phenyl, or halogen, $R^5$ and $R^6$ are H or alkyl.

EP 0 591 528 (Otsuka,1991) discloses anti-inflammatory use of pyrazolopyrimidines represented by the formula

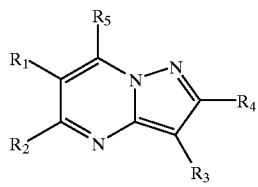

where $R_1$, $R_2$, $R_3$ and $R_4$ are H, carboxyl, alkoxycarbonyl, optionally substituted alkyl, cycloalkyl, or phenyl, $R_5$ is $SR_6$ or $NR_7R_8$, $R_6$ is pyridyl or optionally substituted phenyl, and $R_7$ and $R_8$ are H or optionally substituted phenyl.

Springer et al, J. Med. Chem., 1976, vol. 19, no. 2, 291–296 and Springer U.S. Pat. Nos. 4,021,556 and 3,920,652 disclose pyrazolopyrimidines of the formula

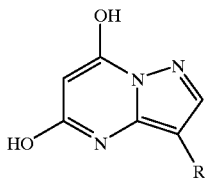

where R can be phenyl, substituted phenyl or pyridyl, and their use to treat gout, based on their ability to inhibit xanthine oxidase.

Joshi et al., J. Prakt. Chemie, 321, 2, 1979, 341–344, discloses compounds of the formula

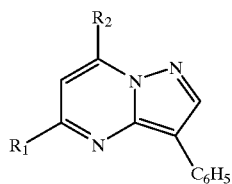

where $R^1$ is $CF_3$, $C_2F_5$, or $C_6H_4F$, and $R^2$ is $CH_3$, $C_2H_5$, $CF_3$, or $C_6H_4F$.

Maquestiau et al., Bull. Soc. Belg., vol.101, no. 2, 1992, pages 131–136 discloses a pyrazolo[1,5-a]pyrimidine of the formula

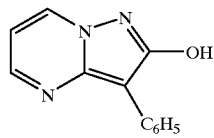

Ibrahim et al., Arch. Pharm. (weinheim) 320, 487–491 (1987) discloses pyrazolo[1,5-a]pyrimidines of the formula

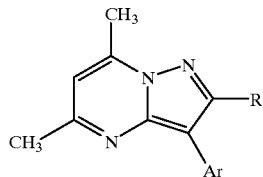

where R is NH2 or OH and Ar is 4-phenyl-3-cyano-2-aminopyrid-2-yl.

Other references which disclose azolopyrimidines included EP 0 511 528 (Otsuka, 1992), U.S. Pat. No. 4,997,940 (Dow, 1991), EP 0 374 448 (Nissan, 1990), U.S. Pat. No. 4,621,556 (ICN,1997), EP 0 531 901 (Fujisawa, 1993), U.S. Pat. No. 4,567,263 (BASF, 1986), EP 0 662 477 (Isagro, 1995), DE 4 243 279 (Bayer, 1994), U.S. Pat. No. 5,397,774 (Upjohn, 1995), EP 0 521 622 (Upjohn, 1993), WO 94/109017 (Upjohn, 1994), J. Med. Chem., 24, 610–613 (1981), and J. Het. Chem., 22, 601 (1985).

SUMMARY OF THE INVENTION

In accordance with one aspect, the present invention provides novel compounds, pharmaceutical compositions and methods which may be used in the treatment of affective disorder, anxiety, depression, irritable bowel syndrome, post-traumatic stress disorder, supranuclear palsy, immune suppression, Alzheimer's disease, gastrointestinal disease, anorexia nervosa or other feeding disorder, drug or alcohol withdrawal symptoms, drug addiction, inflammatory disorder, fertility problems, disorders, the treatment of which can be effected or facilitated by antagonizing CRF, including but not limited to disorders induced or facilitated by CRF, or a disorder selected from inflammatory disorders such as rheumatoid arthritis and osteoarthritis, pain, asthma, psoriasis and allergies; generalized anxiety disorder; panic, phobias, obsessive-compulsive disorder; post-traumatic stress disorder; sleep disorders induced by stress; pain perception such as fibromyalgia; mood disorders such as depression, including major depression, single episode depression, recurrent depression, child abuse induced depression, and postpartum depression; dysthemia; bipolar disorders; cyclothymia; fatigue syndrome; stress-induced headache; cancer, human immunodeficiency virus (HIV) infections; neurodegenerative diseases such as Alzheimer's disease, Parkinson's disease and Huntington's disease; gastrointestinal diseases such as ulcers, irritable bowel syndrome, Crohn's disease, spastic colon, diarrhea, and post operative ilius and colonic hypersensitivity associated by psychopathological disturbances or stress; eating disorders such as anorexia and bulimia nervosa; hemorrhagic stress; stress-induced psychotic episodes; euthyroid sick syndrome; syndrome of inappropriate antidiarrhetic hormone (ADH); obesity; infertility; head traumas; spinal cord trauma;

ischemic neuronal damage (e.g., cerebral ischemia such as cerebral hippocampal ischemia); excitotoxic neuronal damage; epilepsy; cardiovascular and hear related disorders including hypertension, tachycardia and congestive heart failure; stroke; immune dysfunctions including stress induced immune dysfunctions (e.g., stress induced fevers, porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type; multiinfarct dementia; amyotrophic lateral sclerosis; chemical dependencies and addictions (e.g., dependencies on alcohol, cocaine, heroin, benzodiazepines, or other drugs); drug and alcohol withdrawal symptoms; osteoporosis; psychosocial dwarfism and hypoglycemia in a mammal.

The present invention provides novel compounds which bind to corticotropin releasing factor receptors, thereby altering the anxiogenic effects of CRF secretion. The compounds of the present invention are useful for the treatment of psychiatric disorders and neurological diseases, anxiety-related disorders, post-traumatic stress disorder, supranuclear palsy and feeding disorders as well as treatment of immunological, cardiovascular or heart-related diseases and colonic hypersensitivity associated with psychopathological disturbance and stress in a mammal.

According to another aspect, the present invention provides novel compounds of Formula(described below) which are useful as antagonists of the corticotropin releasing factor. The compounds of the present invention exhibit activity as corticotropin releasing factor antagonists and appear to suppress CRF hypersecretion. The present invention also includes pharmaceutical compositions containing such compounds of Formula (1) and methods of using such compounds for the suppression of CRF hypersecretion, and/or for the treatment of anxiogenic disorders.

According to yet another aspect of the invention, the compounds provided by this invention (and especially labelled compounds of this invention) are also useful as standards and reagents in determining the ability of a potential pharmaceutical to bind to the CRF receptor.

DETAILED DESCRIPTION OF INVENTION

[1] In a first embodiment the present invention provides for a compound of Formula (I) or (II)

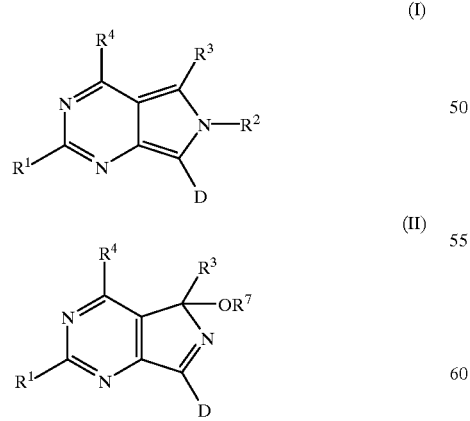

wherein

D is $Ar^1$ or heteroaryl, each optionally substituted with 1 to 5 $R^5$ groups and each is attached to an unsaturated carbon atom;

$R^1$ is H, $Ar^2$, heteroaryl, heterocyclyl, or carbocyclyl; or $C_1$–$C_6$ alkyl, $C_2$–$C_4$ alkenyl, or $C_2$–$C_4$ alkynyl, each optionally substituted with 1 to 3 substituents independently selected at each occurrence from $C_1$–$C_4$ alkyl, $Ar^2$, heteroaryl, heterocyclyl, carbocyclyl, $OR^{12}$, F, Cl, Br, I, $CF_3$, and $NO_2$;

$R^2$ is H, $Ar^2$, heteroaryl, heterocyclyl, or carbocyclyl; or $C_1$–$C_{10}$ alkyl, $C_3$–$C_{10}$ alkenyl, $C_3$–$C_{10}$ alkynyl, each optionally substituted with 1 to 3 substituents independently selected at each occurrence from $C_1$–$C_6$ alkyl, $C_3$–$C_6$ cycloalkyl, $C_1$–$C_4$ haloalkyl, $Ar^2$, heteroaryl, heterocyclyl, carbocyclyl, F, Br, Cl, I, CN, $OR^{12}$, $SR^{15}$, $NO_2$, $NR^9COR^{13}$, $NR^9CONR^{11}R^{10}$, $NR^9CO_2R^{12}$, $NR^{11}R^{10}$ and $CONR^{11}R^{10}$;

$R^3$ is H, $Ar^2$, heteroaryl, heterocyclyl, or carbocyclyl; or $C_1$–$C_{10}$ alkyl, $C_2$–$C_{10}$ alkenyl, $C_2$–$C_{10}$ alkynyl, $C_1$–$C_4$ haloalkyl, each optionally substituted with 1 to 3 substituents independently selected at each occurrence from $C_1$–$C_4$ alkyl, $Ar^2$, heteroaryl, heterocyclyl, carbocyclyl, $NO_2$, F, Cl, Br, I, $NR^9COR^7$, $NR^9CO_2R^7$, $OR^7$, $CONR^{10}R^{11}$, and $CO(NOR^{12})R^7$;

$R^4$ is $NR^{11}R^{10}$;

$R^5$ is independently selected at each occurrence from: $NO_2$, F, Cl, Br, I, CN, $NR^{10}R^{11}$, $NR^9COR^{13}$, $NR^9CO_2R^7$, $COR^{13}$, $R^{13}$, $OR^{12}$, $CONR^{10}R^{11}$, $CO(NOR^9)R^{10}$, $CO_2R^{12}$, and $S(O)_nR^{14}$; or $C_1$–$C_6$ alkyl, $C_2$–$C_{10}$ alkenyl, and $C_2$–C10 alkynyl, each optionally substituted with 1 to 3 substituents independently selected at each occurrence from $C_1$–$C_4$ alkyl, $C_3$–$C_6$ cycloalkyl, $CF_3$, $NO_2$, F, Cl, Br, I, CN, $NR^6R^7$, $NR^9COR^7$, $NR^9CO_2R^7$, $COR^7$, $OR^7$, $CONR^6R^7$, $CO_2R^7$, $CO(NOR^9)R^7$, and $S(O)_nR^7$;

$R^6$ is independently selected at each occurrence from:
 H, —$CH_2Ar^2$, $Ar^2$, heteroaryl, heterocyclyl, and carbocyclyl; or
 $C_1$–$C_{10}$ alkyl, $C_2$–$C_{10}$ alkenyl, $C_2$–$C_{10}$ alkynyl, $C_1$–$C_4$ haloalkyl, each optionally substituted with 1 to 3 substituents independently selected at each occurrence from $C_1$–$C_6$ alkyl, $C_1$–$C_4$ haloalkyl, CN, F, Cl, Br, I, $OR^{12}$, $NO_2$, $S(O)_nR^{14}$, $COR^{13}$, $CO_2R^{12}$, $OC(O)R^{14}$, $NR^9COR^{13}$, $N(COR^{13})_2$, $NR^9CONR^{11}R^{10}$, $NR^9CO_2R^{12}$, $NR^{11}R^{10}$, $CONR^{11}R^{10}$, $Ar^2$, heteroaryl, heterocyclyl, and carbocyclyl;

$R^7$ is independently selected at each occurrence from:
 H, —$CH_2Ar^2$, $Ar^2$, heteroaryl, heterocyclyl, and carbocyclyl; or
 $C_1$–$C_{10}$ alkyl, $C_2$–$C_{10}$ alkenyl, $C_2$–$C_{10}$ alkynyl, $C_1$–$C_4$ haloalkyl, each optionally substituted with 1 to 3 substituents independently selected at each occurrence from $C_1$–$C_6$ alkyl, $C_1$–$C_4$ haloalkyl, CN, F, Cl, Br, I, $OR^{12}$, $NO_2$, $S(O)_nR^{14}$, $COR^{13}$, $CO_2R^{12}$, $OC(O)R^{13}$, $NR^9COR^{13}$, $N(COR^{13})_2$, $NR^9CONR^{11}R^{10}$, $NR^9CO_2R^{12}$, $NR^{11}R^{10}$, $CONR^{11}R^{10}$, $Ar^2$, heteroaryl, heterocyclyl, and carbocyclyl;

$Ar^1$ is phenyl or naphthyl;

$Ar^2$ is phenyl or naphthyl, each optionally substituted with 1 to 5 substituents independently selected at each occurrence from $C_1$–$C_6$ alkyl, $C_3$–$C_6$ cycloalkyl, $C_1$–$C_4$ haloalkyl, CN, F, Cl, Br, I, $OR^{12}$, NO2, S(O)$nR^{14}$, $COR^{13}$, $CO_2R^{12}$, $OC(O)R^{13}$, $NR^9COR^{13}$, $N(COR^{13})_2$, $NR^9CONR^{11}R^{10}$, $NR^9CO_2R^{12}$, $NR^{11}R^{10}$, and $CONR^{11}R^{10}$;

heteroaryl is pyridyl, pyrimidinyl, triazinyl, furanyl, pyrrolyl, imidazolyl, pyranyl, quinolinyl, isoquinolinyl, thienyl, imidazolyl, thiazolyl, indolyl, indazolyl, pyrrolyl, oxazolyl, benzofuranyl, benzothienyl, benzothiazolyl, isoxazolyl, pyrazolyl, 2,3-dihydrobenzothienyl or 2,3-dihydrobenzofuranyl;

heterocyclyl is saturated or partially saturated heteroaryl, optionally substituted with 1 to 5 substituents independently selected at each occurrence from $C_1$–$C_6$ alkyl, $C_3$–$C_6$ cycloalkyl, $C_1$–$C_4$ haloalkyl, CN, F, Cl, Br, I, $OR^{12}$, $NO_2$, $S(O)nR^{14}$, $COR^{13}$, $CO_2R^{12}$, $OC(O)R^{13}$, $NR^9COR^{13}$, $N(COR^{13})_2$, $NR^9CONR^{11}R^{10}$, $NR^9CO_2R^{12}$, $NR^{10}R^{11}$, and $CONR^{11}R^{10}$;

carbocyclyl is saturated or partially unsaturated $C_3$–$C_{10}$ membered ring, optionally substituted with 1 to 5 substituents independently selected at each occurrence from $C_1$–$C_6$ alkyl, $CF_3$, CN, F, Cl, Br, I, $OR^{12}$, $SR^{10}$, $S(O)nR^{14}$, $COR^{13}$, $CO_2R^{12}$, $OC(O)R^{13}$, $NR^9COR^{13}$, $N(COR^{13})_2$, $NR^9CONR^{11}R^{10}$, $NR^9CO_2R^{12}$, $NR^{10}R^{11}$, and $CONR^{11}R^{10}$;

$R^9$ is independently selected at each occurrence from H, $C_1$–$C_4$ alkyl, and $C_3$–$C_6$ cycloalkyl;

$R^{10}$ is H, heterocyclyl, or carbocycle; or
  $C_1$–$C_6$ alkyl, $C_2$–$C_6$ alkenyl, $C_2$–$C_6$ alkynyl, $Ar^2$, heteroaryl, each optionally substituted with 1–3 F, Cl, Br, I, $NO_2$, $CF_3$, CN, or $OR^{12}$;

$R^{11}$ is H, heterocyclyl, or carbocycle; or
  $C_1$–$C_6$ alkyl, $C_2$–$C_6$ alkenyl, and $C_2$–$C_6$ alkynyl, $Ar^2$, heteroaryl, each optionally substituted with 1–3 $C_1$–$C_6$ alkyl, $C_3$–$C_6$ cycloalkyl, F, Cl, Br, I, $NO_2$, $CF_3$, CN, or $OR^{12}$;

alternatively, $R^{10}$ and $R^{11}$ can combine to form piperidine, pyrrolidine, piperazine, N-methylpiperazine, morpholine or thiomorpholine, each optionally substituted with 1–3 $C_1$–$C_4$ alkyl groups;

$R^{12}$ is independently selected at each occurrence from H, $C_1$–$C_6$ alkyl, $C_3$–$C_6$ cycloalkyl, and $C_1$–$C_4$ haloalkyl;

$R^{13}$ is selected from H, $C_1$–$C_4$ alkyl, $C_1$–$C_4$ haloalkyl, $C_1$–$C_4$ alkoxy $C_1$–$C_6$ alkyl, $C_3$–$C_6$ cycloalkyl, and $C_3$–$C_6$ cycloalkyl $C_1$–$C_6$ alkyl;

$R^{14}$ is independently selected at each occurrence from $C_1$–$C_6$ alkyl, $C_3$–$C_6$ alkyl, and phenyl, each subsituted by 1–3 $C_1$–$C_4$ alkyl, $C_1$–$C_4$ haloalkyl or $OR^{15}$; and $R^{15}$ is independently selected at each occurrence from H, $C_1$–$C_6$ alkyl, $C_3$–$C_6$ cycloalkyl, and $C_1$–$C_4$ haloalkyl.

[2] In a more preferred embodiment, the present invention provides for a compound of Formula (Ia),

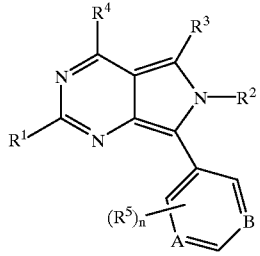

Formula (Ia)

wherein:

A is $CR^{13}$ or N;

B is $CR^{13}$ or N;

n is 0, 1, 2, or 3;

$R^1$ is H; or
  $C_1$–$C_6$ alkyl, $C_2$–$C_4$ alkenyl, $C_2$–$C_4$ alkynyl, each optionally substituted with 1 to 3 substituents independently selected at each occurrence from $C_1$–$C_4$ alkyl, $OR^{12}$, F, Cl, Br, I, $CF_3$, and $NO_2$;

$R^2$ is H; or
  $C_1$–$C_{10}$ alkyl, $C_3$–$C_{10}$ alkenyl, $C_3$–$C_{10}$ alkynyl, each optionally substituted with 1 to 3 substituents independently selected at each occurrence from $C_1$–$C_6$ alkyl, $C_3$–$C_6$ cycloalkyl, $C_1$–$C_4$ haloalkyl, F, Br, Cl, I, CN, $OR^{12}$, $SR^{15}$, $NO_2$, $NR^9COR^{13}$, $NR^9CONR^{11}R^{10}$, $NR^9CO_2R^{12}$, $NR^{11}R^{10}$, and $CONR^{11}R^{10}$;

$R^3$ is H; or
  $C_1$–$C_{10}$ alkyl, $C_2$–$C_{10}$ alkenyl, $C_2$–$C_{10}$ alkynyl, or $C_1$–$C_4$ haloalkyl, each optionally substituted with 1 to 3 substituents independently selected at each occurrence from $C_1$–$C_4$ alkyl, $NO_2$, F, Cl, Br, I, $NR^9COR^7$, $NR^9CO_2R^7$, $OR^7$, $CONR^{10}R^{11}$, or $CO(NOR^{12})R^7$;

$R^4$ is $NR^{10}R^{11}$;

$R^6$ is independently selected at each occurrence from:
  H, —$CH_2Ar^2$, and $Ar^2$; or
  $C_1$–$C_{10}$ alkyl, $C_2$–$C_{10}$ alkenyl, $C_2$–$C_{10}$ alkynyl, and $C_1$–$C_4$ haloalkyl, each optionally substituted with 1 to 3 substituents independently selected at each occurrence from $C_1$–$C_6$ alkyl, $C_1$–$C_4$ haloalkyl, CN, F, Cl, Br, I, $NO_2$, and $OR^{12}$;

$R^7$ is independently selected at each occurrence from:
  H, —$CH_2Ar^2$, and $Ar^2$; or
  $C_1$–$C_{10}$ alkyl, $C_2$–$C_{10}$ alkenyl, $C_2$–$C_{10}$ alkynyl, $C_1$–$C_4$ haloalkyl, each optionally substituted with 1 to 3 substituents independently selected at each occurrence from $C_1$–$C_6$ alkyl, $C_1$–$C_4$ haloalkyl, CN, F. Cl, Br, I, $NO_2$, and $OR^{12}$;

$Ar^2$ is phenyl optionally substituted with 1 to 5 substituents independently selected at each occurrence from $C_1$–$C_6$ alkyl, $C_3$–$C_6$ cycloalkyl, $C_1$–$C_4$ haloalkyl, CN, F, Cl, Br, I, $OR^{12}$, and $NO_2$;

$R^{10}$ is H; or
  $C_1$–$C_6$ alkyl, $C_2$–$C_6$ alkenyl, $C_2$–$C_6$ alkynyl, $Ar^2$, heteroaryl, each optionally substituted with 1–3 F, Cl, Br, I, $NO_2$, $CF_3$, CN, or $OR^{12}$;

$R^{11}$ is H; or
  $C_1$–$C_6$ alkyl, $C_2$–$C_6$ alkenyl, and $C_2$–$C_6$ alkynyl, $Ar^2$, heteroaryl, each optionally substituted with 1–3 $C_1$–$C_6$ alkyl, $C_3$–$C_6$ cycloalkyl, F, Cl, Br, I, $NO_2$, $CF_3$, CN, or $OR^{12}$;

alternatively, $R^{10}$ and $R^{11}$ can combine to form piperidine, pyrrolidine, piperazine, N-methylpiperazine, morpholine or thiomorpholine, each optionally substituted with 1–3 $C_1$–$C_4$ alkyl groups.

[3] In a further more preferred embodiment, the present invention provides for a compound of Formula (Ia),

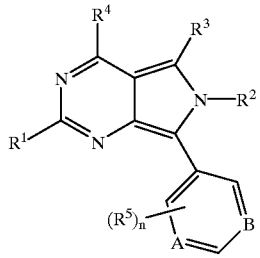

Formula (Ia)

wherein

A is $CR^{13}$;

B is $CR^{13}$;

n is 0, 1, 2, or 3;

$R^1$ is H; or
  $C_1$–$C_4$ alkyl, $C_2$–$C_4$ alkenyl, or $C_2$–$C_4$ alkynyl, each optionally substituted with 1 to 3 substituents independently selected at each occurrence from $C_1$–$C_4$ alkyl, $OR^{12}$, F, Cl, Br, I, $CF_3$, and $NO_2$;

$R^2$ is H; or
  $C_1$–$C_4$ alkyl, $C_2$–$C_4$ alkenyl, $C_2$–$C_4$ alkynyl, each optionally substituted with 1 to 3 substituents independently selected at each occurrence from $C_1$–$C_4$ alkyl, $C_3$–$C_6$ cycloalkyl, $C_1$–$C_4$ haloalkyl, F, Br, Cl, I, CN, $OR^{12}$, $SR^{15}$, $NO_2$, $NR^9CO_2R^{12}$, $NR^{11}R^{10}$, and $CONR^{11}R^{10}$;

$R^3$ is H; or
  $C_1$–$C_4$ alkyl, $C_2$–$C_4$ alkenyl, $C_2$–$C_4$ alkynyl, $C_1$–$C_4$ haloalkyl, each optionally substituted with 1 to 3 substituents independently selected at each occurrence from $C_1$–$C_4$ alkyl, $NO_2$, F, Cl, Br, I, $NR^9COR^7$, $NR^9CO_2R^7$, $OR^7$, $CONR^{10}R^{11}$, and $CO(NOR^{12})R^7$;

$R^4$ is $NR^{10}R^{11}$;

$R^{10}$ is H; or
  $C_1$–$C_6$ alkyl, $C_2$–$C_6$ alkenyl, $C_2$–$C_6$ alkynyl, each optionally substituted with 1–3 F, Cl, Br, I, $NO_2$, $CF_3$, CN, or $OR^{12}$;

$R^{11}$ is H; or $C_1$–$C_6$ alkyl, $C_2$–$C_6$ alkenyl, and $C_2$–$C_6$ alkynyl, each optionally substituted with 1–3 $C_1$–$C_6$ alkyl, $C_3$–$C_6$ cycloalkyl, F, Cl, Br, I, $NO_2$, $CF_3$, CN, or $OR^{12}$;

alternatively, $R^{10}$ and $R^{11}$ can combine to form piperidine, pyrrolidine, piperazine, N-methylpiperazine, morpholine or thiomorpholine, each optionally substituted with 1–3 $C_1$–$C_4$ alkyl groups.

[4] In an even more preferred embodiment, the present invention provides for a compound of Formula (Ib)

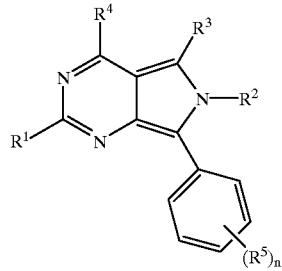

(Ib)

wherein:

n is 1, 2, or 3;

$R^5$ is independently selected at each occurrence from:
  $NO_2$, F, Cl, Br, I, CN, $NR^9COR^{13}$, $NR^9CO_2R^7$, $COR^{13}$, $R^{13}$, $CONR^{10}R^{11}$, $CO(NOR^9)R^{10}$, $CO_2R^{12}$, and $S(O)_nR^{14}$;

$R^4$ is $NR^{10}R^{11}$;

$R^{10}$ is H; or
  $C_1$–$C_4$ alkyl, $C_2$–$C_4$ alkenyl, $C_2$–$C_4$ alkynyl, each optionally substituted with 1–3 F, Cl, Br, I, $NO_2$, $CF_3$, CN, or $OR^{12}$;

$R^{11}$ is H; or
  $C_1$–$C_4$ alkyl, $C_2$–$C_4$ alkenyl, and $C_2$–$C_4$ alkynyl, each optionally substituted with 1–3 $C_1$–$C_4$ alkyl, $C_3$–$C_6$ cycloalkyl, F, Cl, Br, I, $NO_2$, $CF_3$, CN, or $OR^{12}$;

alternatively, $R^{10}$ and $R^{11}$ can combine to form piperidine, pyrrolidine, piperazine, N-methylpiperazine, morpholine or thiomorpholine, each optionally substituted with 1–2 $C_1$–$C_4$ alkyl groups.

[5] In another preferred embodiment, the present invention provides for a compound of Formula (Ic),

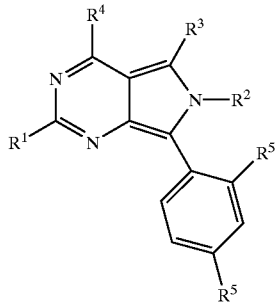

Formula (Ic)

wherein:

$R^5$ is independently selected at each occurrence from:
  $NO_2$, F, Cl, Br, I, CN, and $R^{13}$;

$R^4$ is $NR^{10}R^{11}$;

$R^{10}$ is H; or
  methyl, ethyl, propyl, butyl, ethene, propene, butene, propargyl, each optionally substituted with 1–3 F, Cl, Br, I, $NO_2$, $CF_3$, CN, or $OR^{12}$;

$R^{11}$ is H; or
  methyl, ethyl, propyl, butyl, ethene, propene, each optionally substituted with 1–2 methyl, ethyl, propyl, cyclopropyl, cyclobutyl, cyclopentyl, cyclohexyl, F, Cl, Br, I, $NO_2$, $CF_3$, CN, or $OR^{12}$;

alternatively, $R^{10}$ and $R^{11}$ can combine to form piperidine, pyrrolidine, piperazine, N-methylpiperazine, morpholine or thiomorpholine, each optionally substituted with 1–3 methyl, ethyl, or propyl groups.

[6] In another more preferred embodiment, the present invention provides for a compound of Formula (IIa),

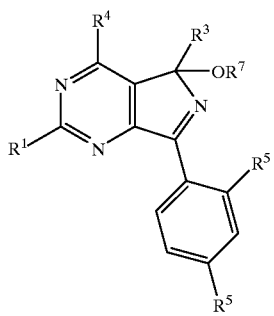

(IIa)

wherein:
$R^1$ is H; or
  $C_1$–$C_6$ alkyl, $C_2$–$C_4$ alkenyl, $C_2$–$C_4$ alkynyl, each optionally substituted with 1 to 3 substituents independently selected at each occurrence from $C_1$–$C_4$ alkyl, $OR^{12}$, F, Cl, Br, I, $CF_3$, and $NO_2$;

$R^3$ is H; or
  $C_1$–$C_{10}$ alkyl, $C_2$–$C_{10}$ alkenyl, $C_2$–$C_{10}$ alkynyl, or $C_1$–$C_4$ haloalkyl, each optionally substituted with 1 to 3 substituents independently selected at each occurrence from $C_1$–$C_4$ alkyl, $NO_2$, F, Cl, Br, I, $NR^9COR^7$, $NR^9CO_2R^7$, $OR^7$, $CONR^{10}R^{11}$, or $CO(NOR^{12})R^7$;

$R^4$ is $NR^{11}R^{10}$;

$R^5$ is independently selected at each occurrence from: $NO_2$, F, Cl, Br, I, CN, and $R^{13}$;

$R^7$ is independently selected at each occurrence from: H, —$CH_2Ar^2$, and $Ar^2$; or
  $C_1$–$C_{10}$ alkyl, $C_2$–$C_{10}$ alkenyl, $C_2$–$C_{10}$ alkynyl, $C_1$–$C_4$ haloalkyl, each optionally substituted with 1 to 3 substituents independently selected at each occurrence from $C_1$–$C_6$ alkyl, $C_1$–$C_4$ haloalkyl, CN, F, Cl, Br, I, $NO_2$, and $OR^{12}$;

$Ar^2$ is phenyl optionally substituted with 1 to 5 substituents independently selected at each occurrence from $C_1$–$C_6$ alkyl, $C_3$–$C_6$ cycloalkyl, $C_1$–$C_4$ haloalkyl, CN, F, Cl, Br, I, $OR^{12}$, and $NO_2$;

$R^9$ is independently selected at each occurrence from H, $C_1$–$C_4$ alkyl, and $C_3$–$C_6$ cycloalkyl;

$R^{10}$ is independently selected at each occurrence from H, $C_1$–$C_6$ alkyl, $C_2$–$C_6$ alkenyl, and $C_2$–$C_6$ alkynyl, each optionally substituted with 1–3 F, Cl, Br, I, $NO_2$, $CF_3$, or $OR^{12}$;

$R^{11}$ is independently selected at each occurrence from H, $C_1$–$C_6$ alkyl, $C_2$–$C_6$ alkenyl, and $C_2$–$C_6$ alkynyl, each optionally substituted with 1–3 $C_1$–$C_6$ alkyl, $C_3$–$C_6$ cycloalkyl, F, Cl, Br, I, $NO_2$, $CF_3$, or $OR^{12}$;

alternatively, $R^{10}$ and $R^{11}$ can combine to form piperidine, pyrrolidine, piperazine, N-methylpiperazine, morpholine or thiomorpholine, each optionally substituted with 1–3 $C_1$–$C_4$ alkyl groups;

$R^{12}$ is independently selected at each occurrence from H, $C_1$–$C_6$ alkyl, $C_3$–$C_6$ cycloalkyl, and $C_1$–$C_4$ haloalkyl;

$R^{13}$ is selected from H, $C_1$–$C_4$ alkyl, $C_1$–$C_4$ haloalkyl, $C_1$–$C_4$ alkoxy $C_1$–$C_6$ alkyl, $C_3$–$C_6$ cycloalkyl, and $C_3$–$C_6$ cycloalkyl $C_1$–$C_6$ alkyl.

[7] In another further more preferred embodiment, the present invention provides for a compound of Formula (IIa), wherein:
$R^5$ is independently selected at each occurrence from: $NO_2$, F, Cl, Br, I, CN, and $R^{13}$;

$R^4$ is $NR^{10}R^{11}$;

$R^{10}$ is H; or
  methyl, ethyl, propyl, butyl, ethene, propene, butene, propargyl, each optionally substituted with 1–3 F, Cl, Br, I, $NO_2$, $CF_3$, CN, or $OR^{12}$;

$R^{11}$ is H; or
  methyl, ethyl, propyl, butyl, ethene, propene, each optionally substituted with 1–2 methyl, ethyl, propyl, cyclopropyl, cyclobutyl, cyclopentyl, cyclohexyl, F, Cl, Br, I, $NO_2$, $CF_3$, CN, or $OR^{12}$;

alternatively, $R^{10}$ and $R^{11}$ can combine to form piperidine, pyrrolidine, piperazine, N-methylpiperazine, morpholine or thiomorpholine, each optionally substituted with 1–3 methyl, ethyl, or propyl groups.

[8] In another even further more preferred embodiment, the compounds of the present invention are selected from:
4-[bis[2-methoxyethyl)amino]-7-(2,4-dichlorophenyl)-2,5,6-trimethylpyrrolo[3,4-d]pyrimidine;
4-[bis[2-methoxyethyl)amino]-7-(2,4-dichlorophenyl)-2,5-dimethylpyrrolo[3,4-d]pyrimidine;
4-(N,N-diethylamino)-7-(2,4-dichlorophenyl)-2,5-dimethyl-pyrrolo[3,4-d]pyrimidine;
4-(N-cyclopropylmethyl-N-propylamino)-7-(2,4-dichlorophenyl)-2,5-dimethyl-pyrrolo[3,4-d]pyrimidine;
4-(N-butyl-N-ethylamino)-7-(2,4-dichlorophenyl)-2,5-dimethylpyrrolo[3,4-d]pyrimidine;
4-[bis(cyclopropylmethyl)amino]7-(2,4-dichlorophenyl)-2,5-dimethylpyrrolo[3,4-d]pyrimidine; and
7-(2,4-Dichloro-phenyl)-4-(1-ethyl-propylamino)-2,5-dimethyl-5H-pyrrolo[3,4-d]pyrimidin-5-ol.

[9] In a second embodiment the present invention provides for a pharmaceutical composition comprising a pharmaceutically acceptable carrier and a therapeutically effective amount of a compound of formula (Ia) or (IIa).

[10] In a third embodiment the present invention provides for a method of treating affective disorder, anxiety, depression in a mammal comprising administering to the mammal a dose of the composition of a compound of Formula (Ia) or (IIa).

Many compounds of this invention have one or more asymmetric centers or planes. Unless otherwise indicated, all chiral (enantiomeric and diastereomeric) and racemic forms are included in the present invention. Many geometric isomers of olefins, C=N double bonds, and the like can also be present in the compounds, and all such stable isomers are contemplated in the present invention. The compounds may be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated.

The term "alkyl" includes both branched and straight-chain alkyl having the specified number of carbon atoms. Commonly used abbreviations have the following meanings: Me is methyl, Et is ethyl, Pr is propyl, Bu is butyl. The prefix "n" means a straight chain alkyl. The prefix "c" means a cycloalkyl. The prefix "(S)" means the S enantiomer and the prefix "(R)" means the R enantiomer. Alkenyl includes hydrocarbon chains of either a straight or branched configuration and one or more unsaturated carbon-carbon bonds which may occur in any stable point along the chain, such as ethenyl, propenyl, and the like. "Alkynyl" includes hydrocarbon chains of either a straight or branched configuration and one or more triple carbon-carbon bonds which may occur in any stable point along the chain, such as ethynyl, propynyl and the like. "Haloalkyl" is intended to include both branched and straight-chain alkyl having the specified number of carbon atoms, substituted with 1 or more halogen; "alkoxy" represents an alkyl group of indicated number of carbon atoms attached through an oxygen bridge; "cycloalkyl" is intended to include saturated ring groups, including mono-, bi- or poly-cyclic ring systems, such as cyclopropyl, cyclobutyl, cyclopentyl, cyclohexyl, and so forth. "Halo" or "halogen" includes fluoro, chloro, bromo, and iodo.

The term "substituted", as used herein, means that one or more hydrogen on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "appropriate amino acid protecting group" means any group known in the art of organic synthesis for the protection of amine or carboxylic acid groups. Such amine protecting groups include those listed in Greene and Wuts, "Protective Groups in Organic Synthesis" John Wiley & Sons, New York (1991) and "The Peptides: Analysis, Synthesis, Biology, Vol. 3, Academic Press, New York (1981), the disclosure of which is hereby incorporated by reference. Any amine protecting group known in the art can be used. Examples of amine protecting groups include, but are not limited to, the following: 1) acyl types such as formyl, trifluoroacetyl, phthalyl, and p-toluenesulfonyl; 2) aromatic carbamate types such as benzyloxycarbonyl (Cbz) and substituted benzyloxy-carbonyls, 1-(p-biphenyl)-1-methylethoxy-carbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl.

The term "pharmaceutically acceptable salts" includes acid or base salts of the compounds of Formulae (1) and (2). Examples of pharmaceutically acceptable salts include, but are not limited to, mineral or organic acid salts of basic residues such as amines; alkali or organic salts of acidic residues such as carboxylic acids; and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

"Prodrugs" are considered to be any covalently bonded carriers which release the active parent drug of formula (I) in vivo when such prodrug is administered to a mammalian subject. Prodrugs of the compounds of formula (I) are prepared by modifying functional groups present in the compounds in such a way that the modifications are cleaved, either in routine manipulation or in vivo, to the parent compounds. Prodrugs include compounds wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups in the compounds of formula (I); and the like.

The term "therapeutically effective amount" of a compound of this invention means an amount effective to antagonize abnormal level of CRF or treat the symptoms of affective disorder, anxiety or depression in a host.

Syntheses

A pyrrolo[3,4-d]pyrimidine of Formula (I') may be prepared from an intermediate X using the procedures outlined in Scheme 1. A compound X may be treated with a halogenating agent in the presence or absence of a base in the presence or absence of an inert solvent at reaction temperatures ranging from −80° C. to 250° C. to give a product XI (where L is halogen). Halogenating agents include, but are not limited to, $Cu(II)L_2$ (L=halogen), $Br_2$, $Cl_2$, $I_2$, N-bromosuccinimide, N-iodosuccinimide or N-chlorosuccinimide. Bases may include, but are not limited to, alkali metal carbonates, alkali metal bicarbonates, trialkyl amines (preferably N,N-di-isopropyl-N-ethyl amine) or aromatic amines (preferably pyridine). Inert solvents may include, but are not limited to, lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide), aromatic hydrocarbons (preferably benzene or toluene), alkyl esters (preferably EtOAc) or haloalkanes of 1 to 10 carbons and 1 to 10 halogens (preferably dichloromethane). Preferred reaction temperatures range from −20° C. to 150° C. The resulting intermediate XI may then be reacted with beta keto ester derivative XII in the presence of a base such as alkali metal alkoxides in a solvent such as aliphatic alcohols or an inert solvent at temperatures ranging from −20° C. to 150° C. to give a product XIII. Inert solvents may include, but are not limited to, polyethers (preferably 1,2-dimethoxyethane), dialkyl ethers (preferably diethyl ether), cyclic ethers (preferably tetrahydro-furan or 1,4-dioxane) or aromatic hydrocarbons (preferably benzene or toluene). Intermediate XIII is treated with a ammonium salts (preferably ammonium acetate) in an organic acid medium (preferably acetic acid) at temperatures ranging from −20° C. to 150° C. to provide a compound XIV. The pyrrole nitrogen of compound XIV may be alkylated using an R²LG group in presence of base in an inert solvent to afford a compound XV. LG is a leaving group which may be a halide, tosylate or a mesylate. Bases may include, but are not limited to, alkali metal hydrides (preferably sodium hydride).
Scheme 1
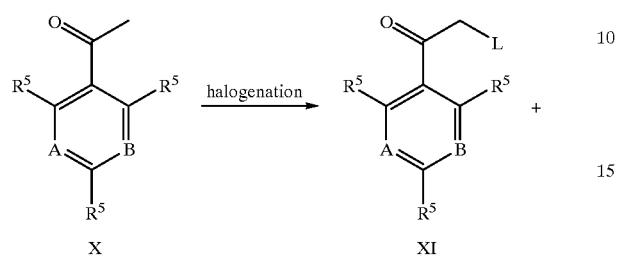
X        XI
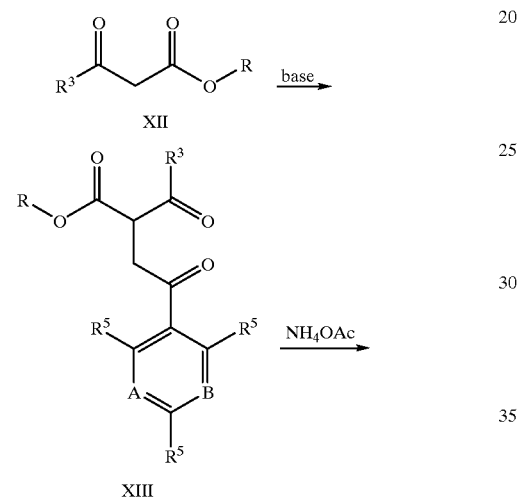
XII
XIII
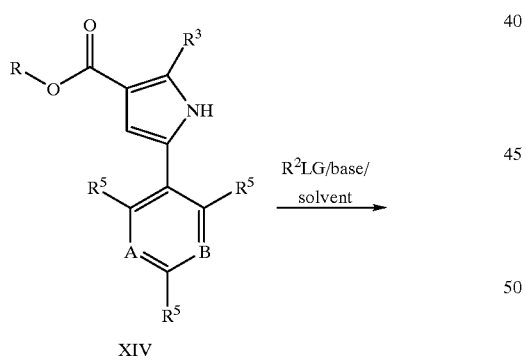
XIV
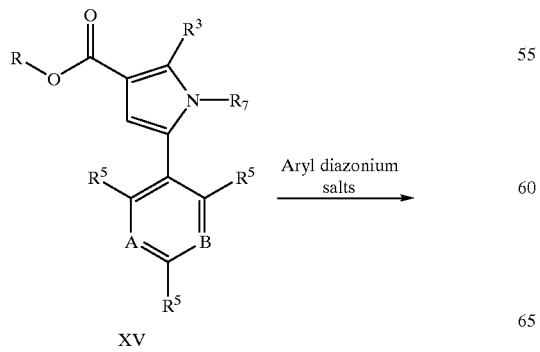
XV
-continued
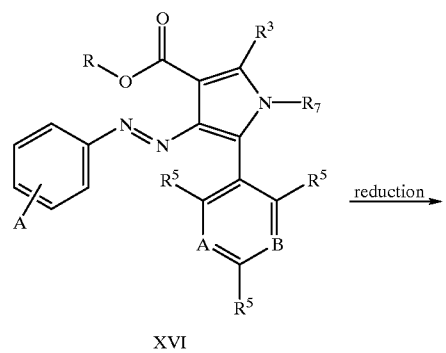
XVI
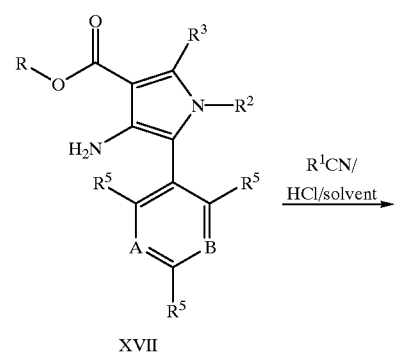
XVII
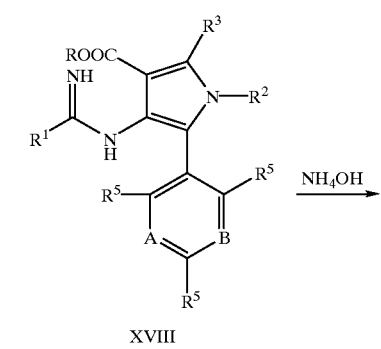
XVIII
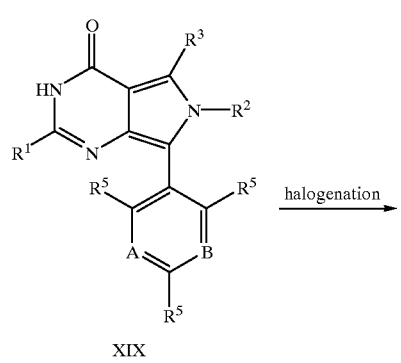
XIX -continued

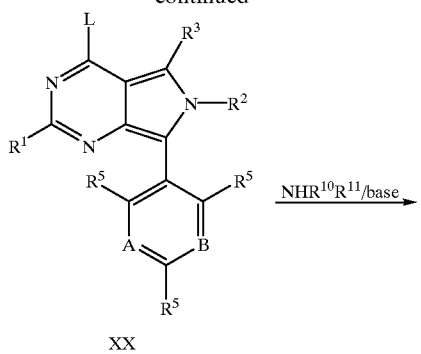

XX

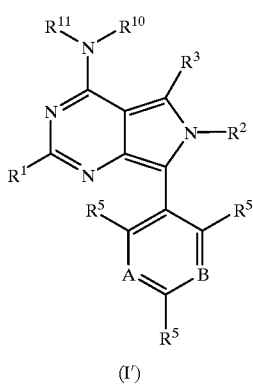

(I')

Inert solvents include, but are not limited to, dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide) or aromatic hydrocarbons (preferably benzene or toluene). Preferred reaction temperatures range from −20° C. to 100° C. The resulting pyrrole derivative XV may be converted to aza derivative XVI by treatment with an aryl diazonium salts in the presence of an alkali metal salts (preferably NaOAc but not limited to) in an acid medium (preferably AcOH but not limited to). The compound of Formula XVI may be reduced to its amino derivative XVII using tin (II) halides (but not limited to) in an acid medium. Acids may include, but are not limited to alkanoic acids of 2 to 10 carbons (preferably acetic acid), haloalkanoic acids (2–10 carbons, 1–10 halogens, such as trifluoroacetic acid), alkanesulfonic acids of 1 to 10 carbons (preferably methanesulfonic acid), hydrochloric acid. Compound XVII may be converted to amidine derivative XVIII by treatment with a nitrile $R^1CN$ in the presence of anhydrous acids (preferably HCl gas but not limited to) in an inert solvent at ambient temperature. Inert solvents may include, but are not limited to, cyclic ethers (preferably tetrahydrofuran or 1,4-dioxane) or aromatic hydrocarbons (preferably benzene or toluene). The amidine derivative XVIII may be cyclized to pyrrolopyrimidone derivative XIX by treatment with either anhydrous or aqeous ammonia in solvents such as aliphatic alcohol. Compound XX may be obtained by treatment of compound XIX with halogenating agents in the presence or absence of a base and inert solvents. Halogenating agents include, but are not limited to, $POCl_3$, $SOCl_2$, $PCl_3$, $PCl_5$ or $PBr_3$. Inert solvents for the halogenation include, but are not limited to, aromatic hydrocarbons (preferably benzene or toluene), or haloalkanes of 1 to 10 carbons and 1 to 10 halogens (preferably dichloromethane). Preferred reaction temperatures range from 0° C. to 150° C. Bases may include, but are not limited to, alkali metal carbonates, alkali metal bicarbonates, trialkyl amines (preferably N,N-di-isopropyl-N-ethyl amine) or aromatic amines (preferably N,N-alkylamines). Compound of the Formula XX may be converted to a compound of present invention (I') by treatment with an amine $HNR^{11}R^{12}$ in the presence or absence of a base as well as in the presence or absence of an inert solvent at temperatures ranging from −80° C. to 150° C.

Alternatively, compounds of the Formula (I') may be obtained from intermediate XXI as described in Scheme 2. An aryl alpha aminonitrile XXII may be prepared by reacting aromatic aldehydes with cyanide reagents, but not limited to trialkylsilylcyanide in the presence of a lewis acids such as zinc iodide (but not limited to) in Scheme 2

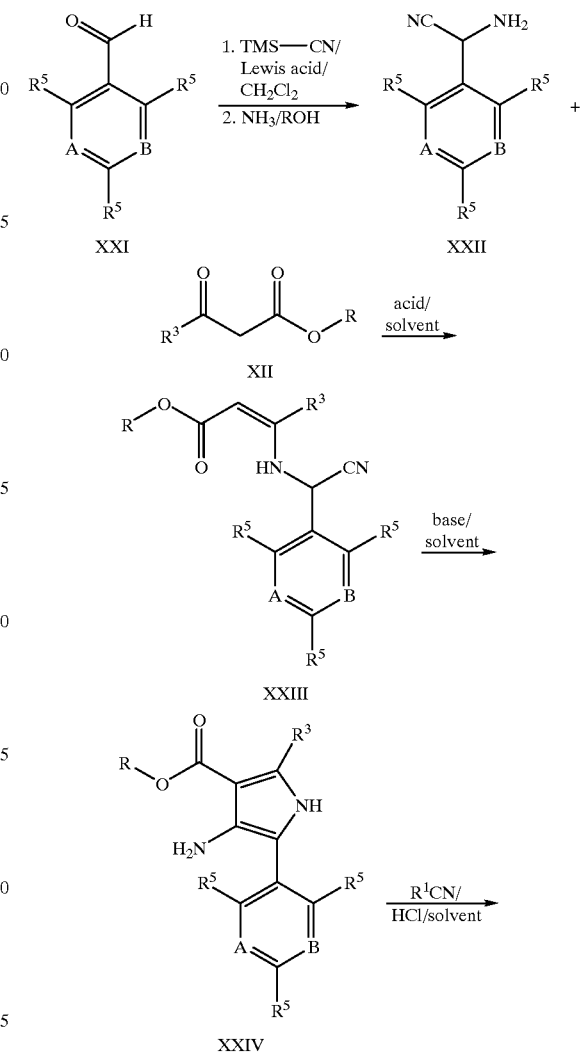

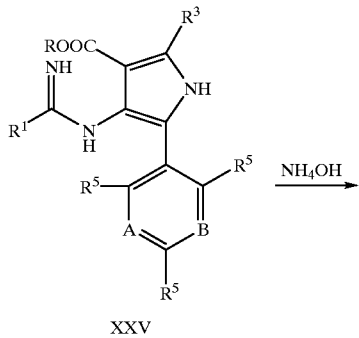

XXV

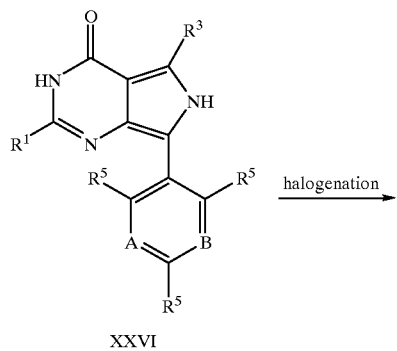

XXVI

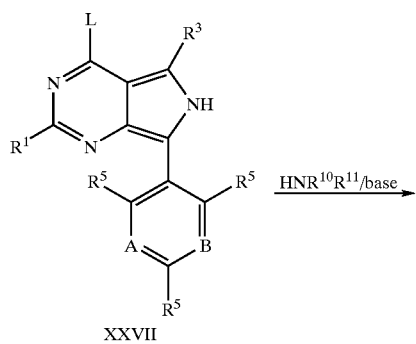

XXVII

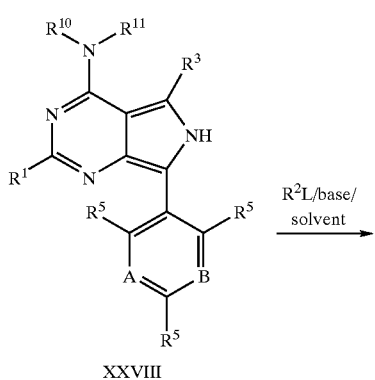

XXVIII

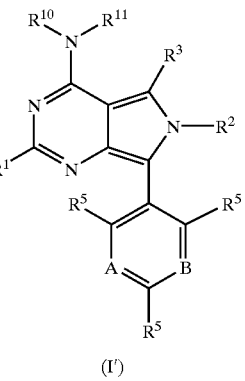

(I')

an inert solvent such as haloalkanes (but not limited to). The resulting silylether derivative may be converted to compounds of Formula XXII by treatment with anhydrous ammonia in aliphatic alcohols (but not limited to). The resulting intermediates XXII may be converted to a compound XXIII by treatment with a beta keto ester derivative XII in the presence of an acid in an inert solvent at temperatures ranging from −20° C. to 150° C. Inert solvents may include, but are not limited to, polyethers (preferably 1,2-dimethoxyethane), dialkyl ethers (preferably diethyl ether), cyclic ethers (preferably tetrahydrofuran or 1,4-dioxane) or aromatic hydrocarbons (preferably benzene or toluene). Acids may include, but are not limited to alkanoic acids of 2 to 10 carbons (preferably acetic acid), haloalkanoic acids (2–10 carbons, 1–10 halogens, such as trifluoroacetic acid), arylsulfonic acids (preferably p-toluenesulfonic acid or benzenesulfonic acid), alkanesulfonic acids of 1 to 10 carbons (preferably methanesulfonic acid) or hydrochloric acid. The pyrrole derivative XXIV may be obtained by treatment of compound XXIII with a base in an inert solvent. Bases may include, but are not limited to, alkali metal hydrides (preferably sodium hydride), alkali metal alkoxides, alkali metal dialkylamides (preferably lithium di-isopropylamide) and alkali metal bis(trialkylsilyl)-amides (preferably sodiumbis(trimethylsilyl) amide). Inert solvents include, but are not limited to, dialkyl ethers (preferably diethyl ether), cyclic ethers (preferably tetrahydrofuran or 1,4-dioxane), aliphatic alcohols, N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide) or aromatic hydrocarbons (preferably benzene or toluene). Compounds XXIV may then be converted to Formula (I') by following similar conditions outlined in Scheme 1.

EXAMPLES

Analytical data were recorded for the compounds described below using the following general procedures.

Proton NMR spectra were recorded on an Varian FT-NMR (300 MHz); chemical shifts were recorded in ppm (δ) from an internal tetramethysilane standard in deuterochloroform or deuterodimethylsulfoxide as specified below. Mass spectra (MS) or high resolution mass spectra (HRMS) were recorded on a Finnegan MAT 8230 spectrometer (using chemical ionization (CI) with $NH_3$ as the carrier gas or gas chromatography (GC) as specified below) or a Hewlett Packard 5988A model spectrometer. Melting points were recorded on a Buchi Model 510 melting point apparatus and are uncorrected. Boiling points are uncorrected. All pH determinations during workup were made with indicator paper.

Reagents were purchased from commercial sources and, where necessary, purified prior to use according to the general procedures outlined by D. Perrin and W. L. F. Armarego, Purification of Laboratory Chemicals, 3rd ed., (New York: Pergamon Press, 1988). Chromatography (thin layer (TLC) or preparative) was performed on silica gel using the solvent systems indicated below. For mixed solvent systems, the volume ratios are given. Otherwise, parts and percentages are by weight.

The following examples are provided to describe the invention in further detail. These examples, which set forth the best mode presently contemplated for carrying out the invention, are intended to illustrate and not to limit the invention.

Example 1

4-[bis[2-methoxyethyl)amino]-7-(2,4-dichlorophenyl)-2,5,6-trimethylpyrrolo[3,4-d]pyrimidine

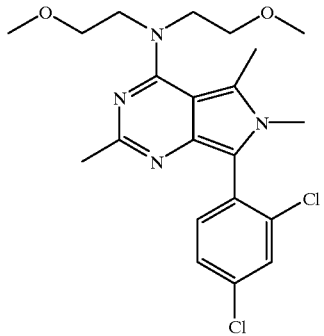

Part A: To an ice cold solution of ethyl acetoacetate (13.0 g, 0.1 mole) in tetrahydrofuran (200 mL) was added dropwise 1.0 M NaHMDS in THF (100 mL, 0.1 mole) over 30 mins under nitrogen atmosphere. After the addition the reaction mixture further stirred at 0° C. for additional 15 mins. To this cold stirred solution was added dropwise 2-bromo-2',4'-dichloroacetophenone (26.0 g, 0.1 mole, prepared according to D. M. Rotstein, D. J. Kertesz, K. A. M. Walker, D. C. Swinney, J. Med. Chem. 1992, 35, 2818–2825) in THF (50 mL) over 15 mins. Stirring was continued for additional 2 h at 0° C. and TLC (dichloromethane) revealed absence of starting material spot (Rf=0.88) and a new spot was noticed (Rf=0.56). The reaction mixture was quenched with water (10 mL) and the solvent was evaporated in vacuo. The residue was diluted with water (500 mL), extracted with EtOAc (3×250 mL), washed the combined organic layers with brine (300 mL) and dried with anhydrous magnesium sulfate. The dried extract was filtered and concentrated in vacuum to afford a residue. The residue was purified by flash column chromatography on a silica gel using dichloromethane as a eluent to afford the dicarbonyl ester derivative (21.3 g, 67% yield) as a pale yellow oil. Anal. calcd. for $C_{14}H_{14}O_4Cl_2$: C, 53.02; H, 4.46. Found: C, 52.95; H, 4.27.

Part B: Ethyl 2-(2,4-dichlorophenyl)-5-methyl-pyrrole carboxylate: The compound of part A of Example 1 (10.8 g, 0.034 moles) in glacial acetic acid (250 mL) was treated with anhydrous ammonium acetate (26.2 g, 0.34 moles, 10 equiv.) and refluxed under nitrogen atmosphere for 48 h. The reaction mixture was then cooled to room temperature and poured over crushed ice (750 g) and stirred for 1 h. The light pink colored solid separated was filtered, dried and purified by flash column chromatography on a silica gel using 0.5% $MeOH/CH_2Cl_2$ as eluent afforded desired pyrrole derivative (9.4 g, mp 144–145° C., 93% yield). Anal. calcd. for $C_{14}H_{13}Cl_2NO_2$: C, 56.40; H, 4.39; N, 4.71. Found: C, 56.11; H, 4.11; N, 4.54.

Part C: Ethyl 2-(2,4-dichlorophenyl)-1,5-dimethyl-pyrrole carboxylate: The compound of part B of Example 1 (5.96 g, 0.02 moles) was dissolved in anhydrous DMF (100 mL) and treated with 60% NaH (0.96 g, 0.024 moles) at 0° C. under nitrogen atmosphere. The mixture was stirred for 15 mins and then treated with excess of iodomethane. The mixture was slowly brought to room temperature and stirred at room temperature for 3 h. TLC (1% $MeOH/CH_2Cl_2$) revealed absence of starting material spot (Rf=0.56) and a new spot was noticed (Rf=0.75). Later the reaction mixture was quenched with ice, extracted with EtOAc (3*75 mL), washed the combined organic layers with brine (50 mL) and dried with anhydrous magnesium sulfate. The dried extract was filtered and concentrated in vacuum to afford a residue. The residue was purified by flash column chromatography on a silica gel using dichloromethane as eluent afforded N-methyl pyrrole derivative (6.0 g, mp 69–70° C., 96% yield) as a white solid. Anal. calcd. for $C_{15}H_{15}Cl_2NO_2$: C, 57.71; H, 4.849; N, 4.50. Found: C, 57.53; H, 4.71; N, 4.35.

Part D: Ethyl 3-amino-2-(2,4-dichlorophenyl)-1,5-dimethylpyrrole carboxylate: To a solution of 4-nitroaniline (2.76 g, 0.02 moles) in 6 N aqeous HCl (15 mL) at −5° C. was added dropwise a solution of $NaNO_2$ (2.25 g, 0.0325 moles) in water (7.5 mL) over 15 mins. After the addition the compound of part C of Example 1 (5.0 g, 0.016 moles) was in dissolved in AcOH (80 mL) and NaOAc (4.0 g)and added to the reaction mixture at 0° C. over 60 mins. Stirring was continued for additional 30 mins at 0° C. and then poured over crushed ice (200 g). The solid separated was filtered, washed with water, dried and purified by flash column chromatography to afford 0.91 g of desired 3-diazapyrrole derivative (17% yield, based on 1.4 g of recovered starting material pyrrole derivative from the column) as red orange liquid. Tin(II) chloride (3.8 g, 20 mmole) was suspended in glacial AcOH (4.0 mL) and heated to 80° C. with stirring. To this mixture was added 3-diazapyrrole derivative (0.91 g, 2.0 mmole) dissolved in AcOH (6.0 mL) over a period of 15 mins. at 80° C. The resultant slurry was stirred for a period of 4 h at 80° C. TLC ($CH_2Cl_2$) indicated absence of starting material (Rf=0.2) and a new spot was noticed (Rf=0.5). The solvent from the reaction mixture was removed and the residue was poured over crushed ice, adjusted the pH to 8 to 9 using dilute NaOH, treated the mixture with 50 mL of EtOAc, filtered the resultant turbid solution over celite, washed the celite with 2×25 mL of EtOAc. The aqeous layer from the filtrate was separated from organic layer, washed with brine (25 mL) and dried (MgSO$_4$). The solvent was stripped in vacuo, and the residue was passed through flash column (eluent: 0.5% methanol/CH$_2$Cl$_2$) and the oil obtained was crystallized from diethyl ether to afford (280 mg, mp 115–116° C., 43% yield) pale yellow crystalline solid. Anal. calcd. for C$_{15}$H$_{16}$Cl$_2$N$_2$O$_2$: C, 55.06; H, 4.949; N,8.56. Found: C, 55.09; H, 4.99; N, 8.50.

Part E: 7-(2,4-Dichlorophenyl)-2,5,6-trimethyl-pyrrolo[3,4-d]pyrimidine-4(3H)-one: The compound of part D of Example 1 (0.25 g, 0.764 mmol) was dissolved in dioxane (2.0 mL) and acetonitrile (2.0 mL) and cooled to 15° C. under nitrogen. Dry HCl (gas) was passed through a syringe needle into the reaction mixture over a period of 4 h. TLC(eluent: 10:1 CH$_2$Cl$_2$/methanol) revealed presence of two new spots at Rf=0.27 and 0.46 (faint) along with unreacted starting material spot at Rf=0.80. Stopped bubbling HCl gas at this stage and allowed to stir at room temp. over night. TLC (eluent: 10:1 CH$_2$Cl$_2$/methanol) revealed absence of starting material spot and also the faint spot at Rf=0.46. The only spot noticed was at Rf=0.27 and mass spectrum revealed formation of acetonitrile addition product (M+H=368). The solvent was removed under vacuum, residue was dissolved in 4.0 mL of 1:1 EtOH/water and basified using 28% ammonium hydroxide to pH 9 to 10. Some solid separation was noticed, but extraction of the mixture with ethyl acetate (15 mL) resulted in separation of white solid. Filtered the solid, washed with ethyl acetate, and dried to afford (0.159 g) desired product. Additional 60 mg of product was obtained by extraction of the aq. layer with EtOAc. Overall yield 0.22 g (88% yield, mp>290° C.). Anal. calcd. for C$_{15}$H$_{13}$Cl$_2$N$_3$O: C, 55.92; H, 4.089; N,13.04. Found: C, 55.77; H, 3.99; N, 12.80.

Part F: 4-Chloro-7-(2,4-dichlorophenyl)-2,5,6-trimethyl-pyrrolo[3,4-d]pyrimidine: The compound of part E of Example 1 (0.125 g, 0.39 mmol) was treated with POCl$_3$ (2.0 mL) and heated at 80° C. for 48 h. Excess POCl$_3$ was removed under vacuum and then quenched with ice (10 g). The reaction mixture was then extracted extracted with EtOAc (3×15 mL), washed the combined organic layers with brine (50 mL) and dried with anhydrous magnesium sulfate. The dried extract was filtered and concentrated in vacuum to afford a residue. The residue was purified by flash column chromatography on a silica gel using 1% MeOH/dichloromethane as eluent to afford corresponding chloro derivative (70 mg, mp 191–192° C., 54% yield) as a yellow solid.

Part G: 4-[bis[2-methoxyethyl)amino]-7-(2,4-dichlorophenyl)-2,5,6-trimethyl-pyrrolo[3,4-d]pyrimidine: The compound of part F of Example 1 (0.57 mg, 0.168 mmol) in ethanol (2.0 mL) was treated with bis (2-methoxyethyl)amine (67 mg, 0.503 mmol, 3 eq.) and heated at 80° C. for 20 h. The reaction mixture was concentrated in vacuum to afford a residue. The residue was purified by flash column chromatography on a silica gel using 2% MeOH/dichloromethane as eluent to afford desired product (43.8 mg, 59% yield) as a yellow oil. HRMS calcd. for C$_{21}$H$_{27}$Cl$_2$N$_4$O$_2$: 437.1511. Found: 437.1497.

Example 2

4-[Bis[2-methoxyethyl)amino]-7-(2,4-dichlorophenyl)-2,5-dimethylpyrrolo[3,4-d]pyrimidine

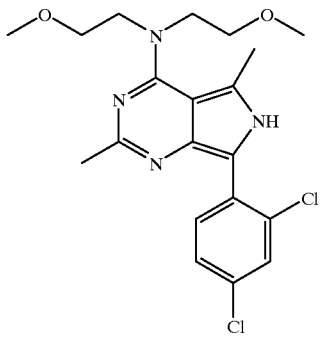

Part A: •-Amino-2,4-dichlorophenylacetonitrile: To a solution of 2,4-dichlorobenzaldehyde (35.0 g, 0.2 moles) in dichloromethane (200.0 mL) was added anhydrous zinc iodide (1.0 g) followed by dropwise addition of TMSCN (25.0 g, 0.25 moles) at room temperature. The resultant mixture was stirred for 30 mins and examination by NMR revealed formation of alpha-silyloxynitrile as a clean product (Product not UV visible). The solvent was evaporated in vacuum and the residue was treated 7.0 M ammonia in methanol (200 mL) and continued the reaction at 40° C. for 16 h. TLC (2% MeOH/CH$_2$Cl$_2$) indicated a new spot (Rf=0.27, visible only with iodine). The solvent was evaporated and the crude was purified by flash column chromatography (eluent CH$_2$Cl$_2$) to afford desired product as a yellow solid (34.75 g, mp 74–75° C., 87% yield). Anal. calcd. for C$_8$H$_6$Cl$_2$N$_2$: C, 47.79; H, 3.02; N, 13.93. Found: C, 47.94; H, 3.12; N, 13.71.

Part B: Ethyl N-(alpha-cyano-2,4-dichlorobenzyl)-3-amino-2-butenoate: To a solution of alpha-amino-2,4-dichlorophenylacetonitrile (20.1 g, 0.1 mole) in benzene (250 mL) was treated with ethyl acetoacetate (13.0 g, 0.1 mole) and p-toluenesulfonic acid monohydrate (0.475 g, 0.0025 mole). The reaction mixture was refluxed for 48 h. TLC (eluent 2% MeOH/CH$_2$Cl$_2$) revealed trace amount of starting material nitrile (Rf=0.27; visible only under iodine) along with a new spot (Rf=0.8). The reaction mixture was cooled to room temp and the solvent was evaporated in vacuo to furnish yellow viscous oil. This crude material was purified using a flash column packed with silica gel and eluted with 10% EtOAc/hexane to afford desired product as yellow oil (19.9 g, 64% yield). Anal. calcd. for C$_{14}$H$_{14}$Cl$_2$N$_2$O$_2$: C, 53.69; H, 4.52; N, 8.94. Found: C, 53.33; H, 4.45; N, 8.56.

Part C: Ethyl 3-amino-2-(2,4-dichlorophenyl)-5-methylpyrrole carboxylate: The compound of part B of Example 2 (19.9 g, 0.0635 moles) in ethanol (200 mL) was added dropwise 21% NaOEt in ethanol (22.6 mL, 0.07 moles) at room temperature. The reaction mixture was further stirred at room temperature for 16 h. TLC (eluent 2% MeOH/CH$_2$Cl$_2$) revealed absence of starting material (Rf= 0.86) and a new spot(Rf=0.33) was noticed. The reaction mixture was diluted with water (300 mL), solid separated was filtered, washed with water and dried in a vacuum oven at 60° C. for 2 days to afford orange yellow solid (15.7 g, mp 150–151° C., 79% yield). Anal. calcd. for C$_{14}$H$_{14}$Cl$_2$N$_2$O$_2$: C, 53.69; H, 4.52; N,8.94. Found: C, 53.44; H, 4.25; N, 9.04.

Part D: 7-(2,4-Dichlorophenyl)-2,5-diimethyl-pyrrolo[3,4-d]pyrimidine-4(3H)-one: The compound of part C of Example 2 (10.0 g, 0.0322 mol) was dissolved in dioxane (100.0 mL) and acetonitrile (100.0 mL) and cooled to 15° C. under nitrogen. Dry HCl (gas) was passed through a syringe needle into the reaction mixture over a period of 30 mins. Stopped bubbling HCl gas at this stage and allowed to stir at room temperature for 20 h. The solvent was removed under vacuum, residue was dissolved in water (150 mL) and basified using 28% ammonium hydroxide to pH 9 to 10. Filtered the solid, washed with water, and dried to afford crude desired product. The crude was treated with hot 2-propanol (150 mL) and filtered the insoluble white solid (7.35 g, mp>260° C., 74% yield). Anal. calcd. for $C_{14}H_{11}Cl_2N_3O$: C, 54.57; H, 3.61; N,13.64. Found: C, 54.20; H, 3.69; N, 13.42.

Part E: 4-Chloro-7-(2,4-dichlorophenyl)-2,5-dimethyl-pyrrolo[3,4-d]pyrimidine: The compound of part D of Example 2 (1.0 g, 3.3 mmol) was treated with $POCl_3$ (7.6 mL) and N,N-diisopropylethylamine (0.66 g, 5.1 mmol). The reaction mixture was heated at 90° C. for 20 h. Excess $POCl_3$ was removed under vacuum and then quenched with ice (50 g). The reaction mixture was then extracted extracted with EtOAc (3×50 mL), washed the combined organic layers with brine (50 mL) and dried with anhydrous magnesium sulfate. The dried extract was filtered and concentrated in vacuum to afford a residue. The residue was purified by flash column chromatography on a silica gel using dichloromethane as eluent to afford corresponding chloro derivative (540 mg, mp 189–190° C., 51% yield) as a yellow solid. Anal. calcd. for $C_{14}H_{10}Cl_3N_3$: C, 51.48; H, 3.10; N,12.87. Found: C, 51.45; H, 3.08; N, 12.79.

Part F: 4-[Bis[2-methoxyethyl)amino]-7-(2,4-dichlorophenyl)-2,5-dimethyl-pyrrolo[3,4-d]pyrimidine hydrochloride salt: The compound of part E of Example 2 (0.1 g, 0.306 mmol) in dichloromethane (10.0 mL) was treated with bis (2-methoxyethyl)amine (123 mg, 0.92 mmol, 3 eq.) and refluxed for 3 days. The reaction mixture was concentrated in vacuum and recrystallized the solid to afford desired product as a yellow solid (HCl salt, 67 mg, mp 235–236° C., 48% yield). Anal. calcd. for $C_{20}H_{25}Cl_3N_4O_2$: C, 52.08; H, 5.46; N, 11.85. Found: C, 52.24; H, 5.48; N, 12.18.

Example 3

4-(N,N-Diethylamino)-7-(2,4-dichlorophenyl)-2,5-dimethyl-pyrrolo[3,4-d]pyrimidine

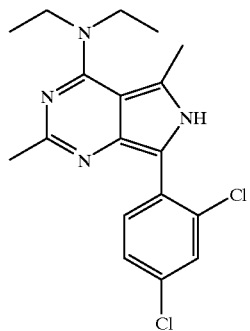

The compound of part E of Example 2 (0.158 g, 0.48 mmol) in dichloromethane (10.0 mL) was treated with N,N-diethylamine (180 mg, 2.4 mmol, 5 eq.) and refluxed for 3 days. The reaction mixture was concentrated in vacuum and purified by flash column chromatography to afford desired product as light brown solid (15 mg, mp 146–148° C.). MS calcd. for $C_{18}H_{20}Cl_2N_4$: 363.29. Found:363 (M+).

Example 4

4-(N-Cyclopropylmethyl-N-propylamino)-7-(2,4-dichlorophenyl)-2,5-dimethyl-pyrrolo[3,4-d]pyrimidine

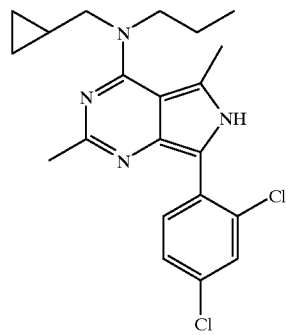

The compound of part E of Example 2 (0.163 g, 0.5 mmol) in ethanol (10.0 mL) was treated with N-propylcyclopropylmethyl-amine (113 mg, 1.0 mmol, 2 eq.) and refluxed for 20 h. The reaction mixture was concentrated in vacuum and purified by flash column chromatography to afford desired product as yellow solid (59 mg, mp 66–68° C., 29% yield). MS calcd. for $C_{21}H_{24}Cl_2N_4$: 403.36. Found: 403 (M+).

Example 5

4-(N-Butyl-N-ethylamino)-7-(2,4-dichlorophenyl)-2,5-dimethylpyrrolo[3,4-d]pyrimidine

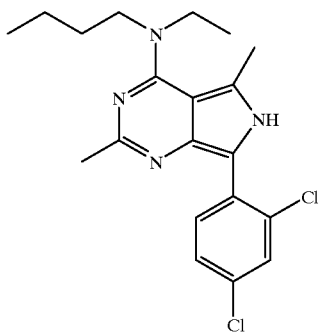

The compound of part E of Example 2 (0.163 g, 0.5 mmol) in ethanol (10.0 mL) was treated with N-ethylbutylamine (101 mg, 1.0 mmol, 2 eq.) and refluxed for 22 h. The reaction mixture was concentrated in vacuum and purified by flash column chromatography to afford desired product as pale yellow solid (120 mg, mp 94–95° C., 62% yield) HRMS calcd. for $C_{20}H_{25}Cl_2N_4$: 391.1456. Found: 391.1456 (M+H).

Example 6

4-[Bis(cyclopropylmethyl)amino]7-(2,4-dichlorophenyl)-2,5-dimethylpyrrolo[3,4-d]pyrimidine

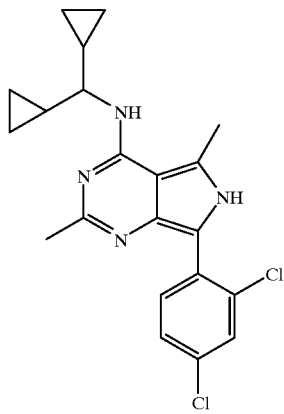

The compound of part E of Example 2 (0.140 g, 0.43 mmol) in ethanol (10.0 mL) was treated with bis(cyclopropyl)methylamine hydrochloride (156 mg, 1.1 mmol) and Hunig's base (0.139 g, 1.1 mmol). The reaction mixture was refluxed for 22 h. The reaction mixture was concentrated in vacuum and crude was treated with EtOAc (2.0 mL). The insoluble pale yellow solid was filtered to afford desired product as a HCl salt (173 mg, mp 218–222° C., 92% yield). HRMS calcd. for $C_{21}H_{23}Cl_2N_4$: 401.1300. Found: 401.1299 (M+H).

Example 7

7-(2,4-Dichloro-phenyl)-4-(1-ethyl-propylamino)-2,5-dimethyl-5H-pyrrolo[3,4-d]pyrimidin-5-ol

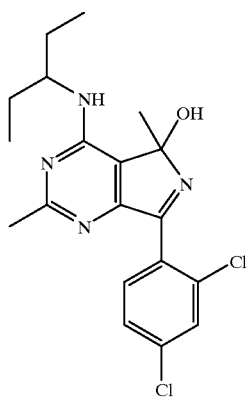

The compound of part E of Example 2 (0.065 g, 0.2 mmol) was treated with 3-pentylamine (0.5 g, 5.8 mmol) and refluxed for 24 h. The reaction mixture was dissolved in dichloromethane (10 mL), washed with water (10 mL) and dried. The dried organic extract was concentrated in vacuum and purified by recrystallization from diethyl ether to afford tertiary alcohol derivative as a white solid (17 mg, mp 184–185° C., 22% yield). NMR (CDCl$_3$): 0.95–1.0 (2 t, 6H, 2×CH$_3$), 1.4–1.75 (m, 4H, 2×CH$_2$), 1.8 (s, 3H, CH$_3$), 2.55 (s, 3H, CH$_3$), 3.55 (bs, 1H, OH), 4.2–4.25 (m, 1H, CH), 4.95 (d, 1H, NH), 7.4 (d, 1H, aromatic H), 7.55 (s, 1H, aromatic H), 7.7–7.5 (d, 1H, aromatic H). MS calcd. for $C_{19}H_{22}Cl_2N_4O$: 393.32. Found: 393 (M+).

Utility

CRF-R1 Receptor Binding Assay for the Evaluation of Biological Activity

The following is a description of the isolation of cell membranes containing cloned human CRF-R1 receptors for use in the standard binding assay as well as a description of the assay itself.

Messenger RNA was isolated from human hippocampus. The mRNA was reverse transcribed using oligo (dt) 12–18 and the coding region was amplified by PCR from start to stop codons. The resulting PCR fragment was cloned into the EcoRV site of PGEMV, from whence the insert was reclaimed using XhoI+XbaI and cloned into the XhoI+XbaI sites of vector pm3ar (which contains a CMV promoter, the SV40 't' splice and early poly A signals, an Epstein-Barr viral origin of replication, and a hygromycin selectable marker). The resulting expression vector, called phchCRFR was transfected in 293EBNA cells and cells retaining the episome were selected in the presence of 400 μM hygromycin. Cells surviving 4 weeks of selection in hygromycin were pooled, adapted to growth in suspension and used to generate membranes for the binding assay described below. Individual aliquots containing approximately 1×10$^8$ of the suspended cells were then centrifuged to form a pellet and frozen.

For the binding assay a frozen pellet described above containing 293EBNA cells transfected with hCRFR1 receptors is homogenized in 10 ml of ice cold tissue buffer (50 mM HEPES buffer pH 7.0, containing 10 mM MgCl$_2$, 2 mM EGTA, 1 μg/l aprotinin, 1 μg/ml leupeptin and 1 μg/ml pepstatin). The homogenate is centrifuged at 40,000×g for 12 min and the resulting pellet rehomogenized in 10 ml of tissue buffer. After another centrifugation at 40,000×g for 12 min, the pellet is resuspended to a protein concentration of 360 μg/ml to be used in the assay.

Binding assays are performed in 96 well plates; each well having a 300 μl capacity. To each well is added 50 μl of test drug dilutions (final concentration of drugs range from 10$^{-10}$–10$^{-5}$ M), 100 μl of $^{125}$I-ovine-CRF ($^{125}$I-o-CRF) (final concentration 150 pM) and 150 μl of the cell homogenate described above. Plates are then allowed to incubate at room temperature for 2 hours before filtering the incubate over GF/F filters (presoaked with 0.3% polyethyleneimine) using an appropriate cell harvester. Filters are rinsed 2 times with ice cold assay buffer before removing individual filters and assessing them for radioactivity on a gamma counter.

Curves of the inhibition of $^{125}$I-o-CRF binding to cell membranes at various dilutions of test drug are analyzed by the iterative curve fitting program LIGAND [P. J. Munson and D. Rodbard, Anal. Biochem. 107:220 (1980), which provides Ki values for inhibition which are then used to assess biological activity.

A compound is considered to be active if it has a K$_i$ value of less than about 10000 nM for the inhibition of CRF.

Inhibition of CRF-Stimulated Adenylate Cyclase Activity

Inhibition of CRF-stimulated adenylate cyclase activity can be performed as described by G. Battaglia et al. Synapse 1:572 (1987). Briefly, assays are carried out at 37° C. for 10 min in 200 ml of buffer containing 100 mM Tris-HCl (pH 7.4 at 37° C.), 10 mM MgCl$_2$, 0.4 mM EGTA, 0.1% BSA, 1 mM isobutylmethylxanthine (IBMX), 250 units/ml phosphocreatine kinase, 5 mM creatine phosphate, 100 mM guanosine 5'-triphosphate, 100 nM OCRF, antagonist peptides (concentration range $10^{-9}$ to $10^{-6m}$) and 0.8 mg original wet weight tissue (approximately 40–60 mg protein). Reactions are initiated by the addition of 1 mM ATP/$^{32}$P] ATP (approximately 2–4 mCi/tube) and terminated by the addition of 100 ml of 50 mM Tris-HCL, 45 mM ATP and 2% sodium dodecyl sulfate. In order to monitor the recovery of cAMP, 1 µl of [$^3$H]cAMP (approximately 40,000 dpm) is added to each tube prior to separation. The separation of [$^{32}$P]cAMP from [$^{32}$P]ATP is performed by sequential elution over Dowex and alumina columns.

In vivo Biological Assay

The in vivo activity of the compounds of the present invention can be assessed using any one of the biological assays available and accepted within the art. Illustrative of these tests include the Acoustic Startle Assay, the Stair Climbing Test, and the Chronic Administration Assay. These and other models useful for the testing of compounds of the present invention have been outlined in C. W. Berridge and A. J. Dunn Brain Research Reviews 15:71 (1990). Compounds may be tested in any species of rodent or small mammal.

Compounds of this invention have utility in the treatment of inbalances associated with abnormal levels of corticotropin releasing factor in patients suffering from depression, affective disorders, and/or anxiety.

Compounds of this invention can be administered to treat these abnormalities by means that produce contact of the active agent with the agent's site of action in the body of a mammal. The compounds can be administered by any conventional means available for use in conjunction with pharmaceuticals either as individual therapeutic agent or in combination of therapeutic agents. They can be administered alone, but will generally be administered with a pharmaceutical carrier selected on the basis of the chosen route of administration and standard pharmaceutical practice.

The dosage administered will vary depending on the use and known factors such as pharmacodynamic character of the particular agent, and its mode and route of administration; the recipient's age, weight, and health; nature and extent of symptoms; kind of concurrent treatment; frequency of treatment; and desired effect. For use in the treatment of said diseases or conditions, the compounds of this invention can be orally administered daily at a dosage of the active ingredient of 0.002 to 200 mg/kg of body weight. Ordinarily, a dose of 0.01 to 10 mg/kg in divided doses one to four times a day, or in sustained release formulation will be effective in obtaining the desired pharmacological effect.

Dosage forms (compositions) suitable for administration contain from about 1 mg to about 100 mg of active ingredient per unit. In these pharmaceutical compositions, the active ingredient will ordinarily be present in an amount of about 0.5 to 95% by weight based on the total weight of the composition.

The active ingredient can be administered orally is solid dosage forms, such as capsules, tablets and powders; or in liquid forms such as elixirs, syrups, and/or suspensions. The compounds of this invention can also be administered parenterally in sterile liquid dose formulations.

Gelatin capsules can be used to contain the active ingredient and a suitable carrier such as but not limited to lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

Liquid dose forms for oral administration can contain coloring or flavoring agents to increase patient acceptance.

In general, water, pharmaceutically acceptable oils, saline, aqueous dextrose (glucose), and related sugar solutions and glycols, such as propylene glycol or polyethylene glycol, are suitable carriers for parenteral solutions. Solutions for parenteral administration preferably contain a water soluble salt of the active ingredient, suitable stabilizing agents, and if necessary, butter substances. Antioxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or propyl-paraben, and chlorobutanol.

Suitable pharmaceutical carriers are described in "Remington's Pharmaceutical Sciences", A. Osol, a standard reference in the field.

Useful pharmaceutical dosage-forms for administration of the compounds of this invention can be illustrated as follows:

Capsules

A large number of units capsules are prepared by filling standard two-piece hard gelatin capsules each with 100 mg of powdered active ingredient, 150 mg lactose, 50 mg cellulose, and 6 mg magnesium stearate.

Soft Gelatin Capsules

A mixture of active ingredient in a digestible oil such as soybean, cottonseed oil, or olive oil is prepared and injected by means of a positive displacement was pumped into gelatin to form soft gelatin capsules containing 100 mg of the active ingredient. The capsules were washed and dried.

Tablets

A large number of tablets are prepared by conventional procedures so that the dosage unit was 100 mg active ingredient, 0.2 mg of colloidal silicon dioxide, 5 mg of magnesium stearate, 275 mg of microcrystalline cellulose, 11 mg of starch, and 98.8 mg lactose. Appropriate coatings may be applied to increase palatability or delayed adsorption.

The compounds of this invention may also be used as reagents or standards in the biochemical study of neurological function, dysfunction, and disease.

Although the present invention has been described and exemplified in terms of certain preferred embodiments, other embodiments will be apparent to those skilled in the art. The invention is, therefore, not limited to the particular embodiments described and exemplified, but is capable of modification or variation without departing from the spirit of the invention, the full scope of which is delineated by the appended claims.

What is claimed is:
1. A compound of Formula (I),

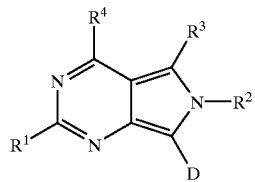

wherein:
- D is $Ar^1$ or heteroaryl, each optionally substituted with 1 to 5 $R^5$ groups and each is attached to an unsaturated carbon atom;
- $R^1$ is H, $Ar^2$, heteroaryl, heterocyclyl, or carbocyclyl; or
  $C_1$–$C_6$ alkyl, $C_2$–$C_4$ alkenyl, or $C_2$–$C_4$ alkynyl, each optionally substituted with 1 to 3 substituents independently selected at each occurrence from $C_1$–$C_4$ alkyl, $Ar^2$, heteroaryl, heterocyclyl, carbocyclyl, $OR^{12}$, F, Cl, Br, I, $CF_3$, and $NO_2$;
- $R^2$ is H, or
  $C_1$–$C_{10}$ alkyl, $C_3$–$C_{10}$ alkenyl, or $C_3$–$C_{10}$ alkynyl, each optionally substituted with 1 to 3 substituents independently selected at each occurrence from $C_1$–$C_6$ alkyl, $C_3$–$C_6$ cycloalkyl, $C_1$–$C_4$ haloalkyl, $Ar^2$, heteroaryl, heterocyclyl, carbocyclyl, F, Br, Cl, I, CN, $OR^{12}$, $SR^{15}$, $NO_2$, $NR^9COR^{13}$, $NR^9CONR^{11}R^{10}$, $NR^9CO_2R^{12}$, $NR^{11}R^{10}$, and $CONR^{11}R^{10}$;
- $R^3$ is H, $Ar^2$, heteroaryl, heterocyclyl, or carbocyclyl; or
  $C_1$–$C_{10}$ alkyl, $C_2$–$C_{10}$ alkenyl, $C_2$–$C_{10}$ alkynyl, or $C_1$–$C_4$ haloalkyl, each optionally substituted with 1 to 3 substituents independently selected at each occurrence from $C_1$–$C_4$ alkyl, $Ar^2$, heteroaryl, heterocyclyl, carbocyclyl, $NO_2$, F, Cl, Br, I, $NR^9COR^7$, $NR^9CO_2R^7$, $OR^7$, $CONR^{10}R^{11}$, and $CO(NOR^{12})R^7$;
- $R^4$ is $NR^{11}R^{10}$;
- $R^5$ is independently selected at each occurrence from: $NO_2$, F, Cl, Br, I, CN, $NR^{10}R^{11}$, $NR^9COR^{13}$, $NR^9CO_2R^7$, $COR^{13}$, $R^{13}$, $OR^{12}$, $CONR^{10}R^{11}$, $CO(NOR^9)R^{10}$, $CO_2R^{12}$, and $S(O)_nR^{14}$ or
  $C_1$–$C_6$ alkyl, $C_2$–$C_{10}$ alkenyl, and $C_2$–$C_{10}$ alkynyl, each optionally substituted with 1 to 3 substituents independently selected at each occurrence from $C_1$–$C_4$ alkyl, $C_3$–$C_6$ cycloalkyl, $CF_3$, $NO_2$, F, Cl, Br, I, CN, $NR^6R^7$, $NR^9COR^7$, $NR^9CO_2R^7$, $COR^7$, $OR^7$, $CONR^6R^7$, $CO_2R^7$, $CO(NOR^9)R^7$, and $S(O)_nR^7$;
- $R^6$ is independently selected at each occurrence from: H, —$CH_2Ar^2$, $Ar^2$, heteroaryl, heterocyclyl, and carbocyclyl; or
  $C_1$–$C_{10}$ alkyl, $C_2$–$C_{10}$ alkenyl, $C_2$–$C_{10}$ alkynyl, and $C_1$–$C_4$ haloalkyl, each optionally substituted with 1 to 3 substituents independently selected at each occurrence from $C_1$–$C_6$ alkyl, $C_1$–$C_4$ haloalkyl, CN, F, Cl, Br, I, $OR^{12}$, $NO_2$, $S(O)_nR^{14}$, $COR^{13}$, $CO2R^{12}$, $OC(O)R^{14}$, $NR^9COR^{13}$, $N(COR^{13})_2$, $NR^9CONR^{11}R^{10}$, $NR^9CO_2R^{12}$, $NR^{11}R^{10}$, $CONR^{11}R^{10}$, $Ar^2$, heteroaryl, heterocyclyl, and carbocyclyl;
- $R^7$ is independently selected at each occurrence from: H, —$CH_2Ar^2$, $Ar^2$, heteroaryl, heterocyclyl, and carbocyclyl; or
  $C_1$–$C_{10}$ alkyl, $C_2$–$C_{10}$ alkenyl, $C_2$–$C_{10}$ alkynyl, and $C_1$–$C_4$ haloalkyl, each optionally substituted with 1 to 3 substituents independently selected at each occurrence from $C_1$–$C_6$ alkyl, $C_1$–$C_4$ haloalkyl, CN, F, Cl, Br, I, $OR^{12}$, $NO_2$, $S(O)_nR^{14}$, $COR^{13}$, $CO_2R^{12}$, $OC(O)R^{13}$, $NR^9COR^{13}$, $N(COR^{13})_2$, $NR^9CONR^{11}R^{10}$, $NR^9CO_2R^{12}$, $NR^{11}R^{10}$, $CONR^{11}R^{10}$, $Ar^2$, heteroaryl, heterocyclyl, and carbocyclyl;
- $Ar^1$ is phenyl or naphthyl;
- $Ar^2$ is phenyl or naphthyl, each optionally substituted with 1 to 5 substituents independently selected at each occurrence from $C_1$–$C_6$ alkyl, $C_3$–$C_6$ cycloalkyl, $C_1$–$C_4$ haloalkyl, CN, F, Cl, Br, I, $OR^{12}$, NO2, $S(O)_nR^{14}$, $COR^{13}$, $CO_2R^{12}$, $OC(O)R^{13}$, $NR^9COR^{13}$, $N(COR^{13})_2$, $NR^9CONR^{11}R^{10}$, $NR^9CO_2R^{12}$, $NR^{11}R^{10}$, and $CONR^{11}R^{10}$;
- heteroaryl is pyridyl, pyrimidinyl, triazinyl, furanyl, pyrrolyl, imidazolyl, pyranyl, quinolinyl, isoquinolinyl, thienyl, imidazolyl, thiazolyl, indolyl, indazolyl, pyrrolyl, oxazolyl, benzofuranyl, benzothienyl, benzothiazolyl, isoxazolyl, pyrazolyl, 2,3-dihydrobenzothienyl or 2,3-dihydrobenzofuranyl;
- heterocyclyl is saturated or partially saturated heteroaryl, optionally substituted with 1 to 5 substituents independently selected at each occurrence from $C_1$–$C_6$ alkyl, $C_3$–$C_6$ cycloalkyl, $C_1$–$C_4$ haloalkyl, CN, F, Cl, Br, I, $OR^{12}$, $NO_2$, $S(O)_nR^{14}$, $COR^{13}$, $CO_2R^{12}$, $OC(O)R^{13}$, $NR^9COR^{13}$, $N(COR^{13})_2$, $NR^9CONR^{11}R^{10}$, $NR^9CO_2R^{12}$, $NR^{10}R^{11}$, and $CONR^{11}R^{10}$;
- carbocyclyl is a saturated or partially unsaturated $C_3$–$C_{10}$ membered ring, optionally substituted with 1 to 5 substituents independently selected at each occurrence from $C_1$–$C_6$ alkyl, $CF_3$, CN, F, Cl, Br, I, $OR^{12}$, $SR^{10}$, $S(O)_nR^{14}$, $COR^{13}$, $CO_2R^{12}$, $OC(O)R^{13}$, $NR^9COR^{13}$, $N(COR^{13})_2$, $NR^9CONR^{11}R^{10}$, $NR^9CO_2R^{12}$, $NR^{10}R^{11}$, and $CONR^{11}R^{10}$;
- $R^9$ is independently selected at each occurrence from H, $C_1$–$C_4$ alkyl, and $C_3$–$C_6$ cycloalkyl;
- $R^{10}$ is H, heterocyclyl, or carbocycle; or
  $C_1$–$C_6$ alkyl, $C_2$–$C_6$ alkenyl, $C_2$–$C_6$ alkynyl, $Ar^2$, or heteroaryl, each optionally substituted with 1–3 F, Cl, Br, I, $NO_2$, $CF_3$, CN, or $OR^{12}$;
- $R^{11}$ is H, heterocyclyl, or carbocycle; or
  $C_1$–$C_6$ alkyl, $C_2$–$C_6$ alkenyl, $C_2$–$C_6$ alkynyl, $Ar^2$, or heteroaryl, each optionally substituted with 1–3 $C_1$–$C_6$ alkyl, $C_3$–$C_6$ cycloalkyl, F, Cl, Br, I, $NO_2$, $CF_3$, CN, or $OR^{12}$;
- alternatively, $R^{10}$ and $R^{11}$ can combine to form piperidine, pyrrolidine, piperazine, N-methylpiperazine, morpholine or thiomorpholine, each optionally substituted with 1–3 $C_1$–$C_4$ alkyl groups;
- $R^{12}$ is independently selected at each occurrence from H, $C_1$–$C_6$ alkyl, $C_3$–$C_6$ cycloalkyl, and $C_1$–$C_4$ haloalkyl;
- $R^{13}$ is selected from H, $C_1$–$C_4$ alkyl, $C_1$–$C_4$ haloalkyl, $C_1$–$C_4$ alkoxy $C_1$–$C_6$ alkyl, $C_3$–$C_6$ cycloalkyl, and $C_1$–$C_6$ alkyl;
- $R^{14}$ is independently selected at each occurrence from $C_1$–$C_6$ alkyl, $C_3$–$C_6$ alkyl, and phenyl, each subsituted by 1–3 $C_1$–$C_4$ alkyl, $C_1$–$C_4$ haloalkyl or $OR^{15}$; and
- $R^{15}$ is independently selected at each occurrence from H, $C_1$–$C_6$ alkyl, $C_3$–$C_6$ cycloalkyl, and $C_1$–$C_4$ haloalkyl.

2. A compound according to claim 1 of Formula (Ia):

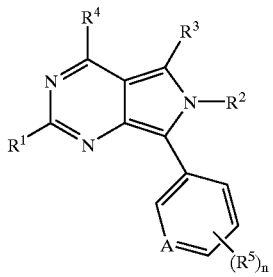

(Ia)

wherein:
A is $CR^{13}$ or N;
B is $CR^{13}$ or N;
n is 0, 1, 2, or 3;
$R^1$ is H; or
$C_1$–$C_6$ alkyl, $C_2$–$C_4$ alkenyl, or $C_2$–$C_4$ alkynyl, each optionally substituted with 1 to 3 substituents independently selected at each occurrence from $C_1$–$C_4$ alkyl, $OR^{12}$, F, Cl, Br, I, $CF_3$, and $NO_2$;
$R^2$ is H ; or
$C_1$–$C_{10}$ alkyl, $C_3$–$C_{10}$ alkenyl, or $C_3$–$C_{10}$ alkynyl, each optionally substituted with 1 to 3 substituents independently selected at each occurrence from $C_1$–$C_6$ alkyl, $C_3$–$C_6$ alkyl, $C_3$–$C_6$ cycloalkyl, $C_1$–$C_4$ haloalkyl, F, Br, Cl, I, CN, $OR^{12}$, $SR^{15}$, $NO_2$, $NR^9COR^{13}$, $NR^9CONR^{11}R^{10}$, $NR^9CO_2R^{12}$, $NR^{11}R^{10}$, and $CONR^{11}R^{10}$;
$R^3$ is H; or
$C_1$–$C_{10}$ alkyl, $C_2$–$C_{10}$ alkenyl, $C_2$–$C_{10}$ alkynyl, or $C_1$–$C_4$ haloalkyl, each optionally substituted with 1 to 3 substituents independently selected at each occurrence from $C_1$–$C_4$ alkyl, $NO_2$, F, Cl, Br, I, $NR^9COR^7$, $NR^9CO_2R^7$, $OR^7$, $CONR^{10}R^{11}$, or $CO(NOR^{12})R^7$;
$R^4$ is $NR^{10} R^{11}$;
$R^6$ is independently selected at each occurrence from: H, —$CH_2Ar^2$, and $Ar^2$; or
$C_1$–$C_{10}$ alkyl, $C_2$–$C_{10}$ alkenyl, $C_2$–$C_{10}$ alkynyl, and $C_1$–$C_4$ haloalkyl, each optionally substituted with 1 to 3 substituents independently selected at each occurrence from $C_1$–$C_6$ alkyl, $C_1$–$C_4$ haloalkyl, CN, F, Cl, Br, I, $NO_2$, and $OR^{12}$;
$R^7$ is independently selected at each occurrence from: H, —$CH_2Ar^2$, and $Ar^2$; or
$C_1$–$C_{10}$ alkyl, $C_2$–$C_{10}$ alkenyl, $C_2$–$C_{10}$ alkynyl, and $C_1$–$C_4$ haloalkyl, each optionally substituted with 1 to 3 substituents independently selected at each occurrence from $C_1$–$C_6$ alkyl, $C_1$–$C_4$ haloalkyl, CN, F, Cl, Br, I, $NO_2$, and $OR^{12}$; $Ar^2$ is phenyl optionally substituted with 1 to 5 substituents independently selected at each occurrence from $C_1$–$C_6$ alkyl, $C_3$–$C_6$ cycloalkyl, $C_1$–$C_4$ haloalkyl, CN, F, Cl, Br, I, $OR^{12}$, and $NO_2$;
$R^{10}$ is H; or
$C_1$–$C_6$ alkyl, $C_2$–$C_6$ alkenyl, $C_2$–$C_6$ alkynyl, $Ar^2$, or heteroaryl, each optionally substituted with 1–3 F, Cl, Br, I, $NO_2$, $CF_3$, CN, or $OR^{12}$;
$R^{11}$ is H; or
$C_1$–$C_6$ alkyl, $C_2$–$C_6$ alkenyl, $C_2$–$C_6$ alkynyl, $Ar^2$, or heteroaryl, each optionally substituted with 1–3 $C_1$–$C_6$ alkyl, $C_3$–$C_6$ cycloalkyl, F, Cl, Br, I, $NO_2$, $CF_3$, CN, or $OR^{12}$;
alternatively, $R^{10}$ and $R^{11}$ can combine to form piperidine, pyrrolidine, piperazine, N-methylpiperazine, morpholine or thiomorpholine, each optionally substituted with 1–3 $C_1$–$C_4$ alkyl groups.

3. A compound of claim 2 wherein:
A is $CR^{13}$;
B is $CR^{13}$;
n is 0, 1, 2, or 3;
$R^1$ is H; or
$C_1$–$C_4$ alkyl, $C_2$–$C_4$ alkenyl, or $C_2$–$C_4$ alkynyl, each optionally substituted with 1 to 3 substituents independently selected at each occurrence from $C_1$–$C_4$ alkyl, $OR^{12}$, F, Cl, Br, I, $CF_3$, and $NO_2$;
$R^2$ is H; or
$C_1$–$C_4$ alkyl, $C_2$–$C_4$ alkenyl, or $C_2$–$C_4$ alkynyl, each optionally substituted with 1 to 3 substituents independently selected at each occurrence from $C_1$–$C_4$ alkyl, $C_3$–$C_6$ cycloalkyl, $C_1$–$C_4$ haloalkyl, F, Br, Cl, I, CN, $OR^{12}$, $SR^{15}$, $NO_2$, $NR^9CO_2R^{12}$, $NR^{11}R^{10}$, and $CONR^{11}R^{10}$;
$R^3$ is H; or
$C_1$–$C_4$ alkyl, $C_2$–$C_4$ alkenyl, $C_2$–$C_4$ alkynyl, or $C_1$–$C_4$ haloalkyl, each optionally substituted with 1 to 3 substituents independently selected at each occurrence from $C_1$–$C_4$ alkyl, $NO_2$, F, Cl, Br, I, $NR^9COR^7$, $NR^9CO_2R^7$, $OR^7$, $CONR^{10} R^{11}$, and $CO(NOR^{12})R^7$;
$R^4$ is $NR^{10} R^{11}$;
$R^{10}$ is H; or
$C_1$–$C_6$ alkyl, $C_2$–$C_6$ alkenyl, or $C_2$–$C_6$ alkynyl, each optionally substituted with 1–3 F, Cl, Br, I, $NO_2$, $CF_3$, CN, or $OR^{12}$;
$R^{11}$ is H; or
$C_1$–$C_6$ alkyl, $C_2$–$C_6$ alkenyl, or $C_2$–$C_6$ alkynyl, each optionally substituted with 1–3 $C_1$–$C_6$ alkyl, $C_3$–$C_6$ cycloalkyl, F, Cl, Br, I, $NO_2$, $CF_3$, CN, or $OR^{12}$;
alternatively, $R^{10}$ and $R^{11}$ can combine to form piperidine, pyrrolidine, piperazine, N-methylpiperazine, morpholine or thiomorpholine, each optionally substituted with 1–3 $C_1$–$C_4$ alkyl groups.

4. A compound of claim 1 of Formula (Ib):

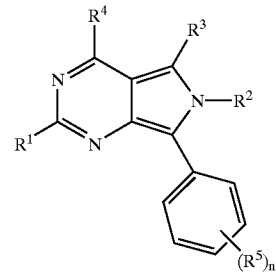

(Ib)

wherein:
n is 1,2, or 3;
$R^5$ is independently selected at each occurrence from: $NO_2$, F, Cl, Br, I, CN, $NR^9COR^{13}$, $NR^9CO_2R^7$, $COR^{13}$, $R^{13}$, $CONR^{10} R^{11}$, $CO(NOR^9)R^{10}$, $CO_2R^{12}$, and $S(O)_nR^{14}$;
$R^4$ is $NR^{10} R^{11}$;
$R^{10}$ is H; or
$C_1$–$C_4$ alkyl, $C_2$–$C_4$ alkenyl, or $C_2$–$C_4$ alkynyl, each optionally substituted with 1–3 F, Cl, Br, I, $NO_2$, $CF_3$, CN, or $OR^{12}$;

$R^{11}$ is H; or $C_1$–$C_4$ alkyl, $C_2$–$C_4$ alkenyl, or $C_2$–$C_4$ alkynyl, each optionally substituted with 1–3 $C_1$–$C_4$ alkyl, $C_3$–$C_6$ cycloalkyl, F, Cl, Br, I, $NO_2$, $CF_3$, CN, or $OR^{12}$;

alternatively, $R^{10}$ and $R^{11}$ can combine to form piperidine, pyrrolidine, piperazine, N-methylpiperazine, morpholine or thiomorpholine, each optionally substituted with 1–2 $C_1$–$C_4$ alkyl groups.

5. A compound of claim 1 of Formula (Ic):

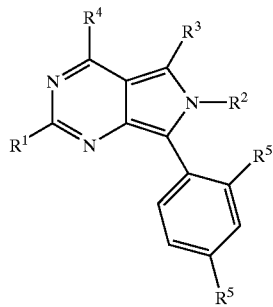

(Ic)

wherein:

$R^5$ is independently selected at each occurrence from: $NO_2$, F, Cl, Br, I, CN, and $R^{13}$;

$R^4$ is $NR^{10}R^{11}$;

$R^{10}$ is H; or methyl, ethyl, propyl, butyl, ethene, propene, butene, or propargyl, each optionally substituted with 1–3 F, Cl, Br, I, $NO_2$, $CF_3$, CN, or $OR^{12}$;

$R^{11}$ is H; or methyl, ethyl, propyl, butyl, ethene, or propene, each optionally substituted with 1–2 methyl, ethyl, propyl, cyclopropyl, cyclobutyl, cyclopentyl, cyclohexyl, F, Cl, Br, I, $NO_2$, $CF_3$, CN, or $OR^{12}$;

alternatively, $R^{10}$ and $R^{11}$ can combine to form piperidine, pyrrolidine, piperazine, N-methylpiperazine, morpholine or thiomorpholine, each optionally substituted with 1–3 methyl, ethyl, or propyl groups.

6. A compound of claim 1 selected from the group consisting of:

4-[bis[2-methoxyethyl)amino]-7-(2,4-dichlorophenyl)-2,5,6-trimethylpyrrolo[3,4-d]pyrimidine;

4-[bis[2-methoxyethyl)amino]-7-(2,4-dichlorophenyl)-2,5-dimethylpyrrolo[3,4-d]pyrimidine;

4-(N,N-diethylamino]-7-(2,4-dichlorophenyl)-2,5-dimethyl-pyrrolo[3,4-d]pyrimidine;

4-(N-cyclopropylmethyl-N-propylamino]-7-(2,4-dichlorophenyl)-2,5-dimethyl-pyrrolo[3,4-d]pyrimidine;

4-(N-butyl-N-ethylamino]-7-(2,4-dichlorophenyl)-2,5-dimethylpyrrolo[3,4-d]pyrimidine;

4-[bis(cyclopropylmethyl)amino]7-(2,4-dichlorophenyl)-2,5-dimethylpyrrolo[3,4-d]pyrimidine; and 7-(2,4-Dichloro-phenyl)-4-(1-ethyl-propylamino)-2,5-dimethyl-5H-pyrrolo[3,4-d]pyrimidin-5-ol.

7. A pharmaceutical composition comprising a pharmaceutically acceptable carrier and a therapeutically effective amount of a compound of claim 1.

8. A method of treating anxiety or depression in a mammal comprising administering to the mammal a dose of a composition according to claim 7.

* * * * *